(12) United States Patent
Bloomfield et al.

(10) Patent No.: US 8,017,608 B2
(45) Date of Patent: Sep. 13, 2011

(54) 5-PHENYLTHIAZOLE DERIVATIVES AND THEIR USE AS P13 KINASE INHIBITORS

(75) Inventors: Graham Charles Bloomfield, Horsham (GB); Ian Bruce, Horsham (GB); Catherine Leblanc, Horsham (GB); Mrinalini Sachin Oza, Horsham (GB); Lewis Whitehead, Marblehead, MA (US); Bernard Cuenoud, Basel (CH); Thomas Hugo Keller, Singapore (SG); Louise Kirman, Cambridge, MA (US); Clive McCarthy, Basel (CH); Gaynor Elizabeth Woodward, Horsham (GB)

(73) Assignee: Novartis AG, Basel (CH)

( * ) Notice: Subject to any disclaimer, the term of this patent is extended or adjusted under 35 U.S.C. 154(b) by 1414 days.

(21) Appl. No.: 10/547,691

(22) PCT Filed: Mar. 5, 2004

(86) PCT No.: PCT/EP2004/002285
§ 371 (c)(1),
(2), (4) Date: Oct. 12, 2005

(87) PCT Pub. No.: WO2004/078754
PCT Pub. Date: Sep. 16, 2004

(65) Prior Publication Data
US 2006/0148822 A1    Jul. 6, 2006

(30) Foreign Application Priority Data
Mar. 6, 2003  (GB) ................... 0305152.1

(51) Int. Cl.
| | |
|---|---|
| *A61K 31/5377* | (2006.01) |
| *A61K 31/497* | (2006.01) |
| *A61K 31/506* | (2006.01) |
| *A61K 31/4523* | (2006.01) |
| *A61K 31/41* | (2006.01) |
| *A61K 31/426* | (2006.01) |
| *A61K 31/427* | (2006.01) |
| *C07D 413/02* | (2006.01) |
| *C07D 401/02* | (2006.01) |
| *C07D 403/02* | (2006.01) |
| *C07D 285/12* | (2006.01) |

(52) U.S. Cl. ........... 514/235.8; 514/252.12; 514/255.05; 514/256; 514/326; 514/363; 514/365; 544/120; 544/132; 544/133; 544/333; 544/366; 544/405; 546/269.7; 548/136; 548/146

(58) Field of Classification Search ............... 546/269.7; 544/405, 120, 132, 133, 333, 366; 548/190, 548/136, 146; 514/252.13, 342, 370, 235.8, 514/252.12, 255.05, 256, 326, 363, 365
See application file for complete search history.

(56) References Cited

FOREIGN PATENT DOCUMENTS
| | | |
|---|---|---|
| WO | 01/17995 | 3/2001 |
| WO | 01/53266 | 7/2001 |
| WO | 03/072557 | 9/2003 |

OTHER PUBLICATIONS

U.S. Application Publication No. 2003/0064996 to Bilodeau et al, published 2003.*
Agullo et al., "Relationship Between Flavonoid Structure and Inhibition of Phosphatidylinositol 3-Kinase: A Comparison with Tyrosine Kinase and Protein Kinase C Inhibition", Biochemical Pharmacology, vol. 53, No. 11, pp. 1649-1657 (1997).

\* cited by examiner

*Primary Examiner* — Rebecca Anderson
*Assistant Examiner* — Samantha Shterengarts
(74) *Attorney, Agent, or Firm* — Paul D. Strain; Strain & Strain PLLC

(57) ABSTRACT

Compounds of formula I

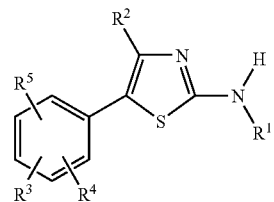

in free or salt form, wherein $R^1$, $R^2$, $R^3$, $R^4$ and $R^5$ have the meanings as indicated in the specification, are useful for treating diseases mediated by phosphatidylinositol 3-kinase. Pharmaceutical compositions that contain the compounds and processes for preparing the compounds are also described.

8 Claims, No Drawings

5-PHENYLTHIAZOLE DERIVATIVES AND THEIR USE AS P13 KINASE INHIBITORS

The present invention relates to organic compounds, their preparation and their use as pharmaceuticals.

In a first aspect, the present invention provides compounds of formula I

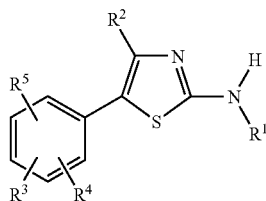

in free or salt form, wherein
$R^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_8$-alkyl optionally substituted by —$NR^6R^7$, carboxy, $C_1$-$C_8$-alkoxy-carbonyl or a 5 or 6-membered heterocyclic ring containing at least one hetero atom selected from the group consisting of nitrogen, oxygen and sulphur, $C_1$-$C_8$-alkoxy, —$NR^6R^7$, $C_3$-$C_8$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_8$-alkyl;
$R^2$ is $C_1$-$C_8$-alkyl or halo;
$R^3$ is hydroxy, halo, $C_1$-$C_8$-alkoxy, $C_1$-$C_8$-alkylcarbonyl, —$SO_2NR^8R^9$, —$SOR^{10}$ or —$SO_2R^{11}$, carboxy, aminocarbonyl, di($C_1$-$C_8$-alkyl)aminocarbonyl, —$NO_2$ or cyano and is in the para or meta position with respect to the indicated thiazole ring;
$R^4$ and $R^5$ are each independently hydrogen, $C_1$-$C_8$-alkyl, $C_1$-$C_8$-alkoxy optionally substituted by a 5 or 6-membered heterocyclic ring containing at least one hetero atom selected from the group consisting of nitrogen, oxygen and sulphur, halo, halo-$C_1$-$C_8$-alkyl, cyano, —$SO_2NH_2$, carboxy, amino, amino-$C_1$-$C_8$-alkyl, di($C_1$-$C_8$-alkyl)amino-$C_1$-$C_8$-alkyl, amino-$C_1$-$C_8$-alkoxy, di($C_1$-$C_8$-alkyl)amino-$C_1$-$C_8$-alkoxy, aminocarbonyl, $C_1$-$C_8$-alkylaminocarbonyl, di($C_1$-$C_8$-alkyl)aminocarbonyl, —$NR^{12}R^{13}$, carboxy-$C_1$-$C_8$-alkyl, carboxy-$C_1$-$C_8$-alkoxy, $R^{14}$, —$OR^{14}$ or a 5 or 6-membered heterocyclic ring containing at least one hetero atom selected from the group consisting of nitrogen, oxygen and sulphur, that ring being optionally substituted by $C_1$-$C_8$-alkyl;
$R^6$ is hydrogen or $C_1$-$C_8$-alkyl;
$R^7$ is $C_1$-$C_8$-alkyl optionally substituted by hydroxy, $C_1$-$C_8$-alkoxy, di($C_1$-$C_8$-alkyl)amino or a 5 or 6-membered heterocyclic ring containing at least one hetero atom selected from the group consisting of nitrogen, oxygen and sulphur, that ring being optionally substituted by $C_1$-$C_8$-alkyl;
$R^8$ is hydrogen or $C_1$-$C_8$-alkyl optionally substituted by hydroxy, $C_1$-$C_8$-alkoxy, cyano, amino, $C_1$-$C_8$-alkylamino, di($C_1$-$C_8$-alkyl)amino or a 5 or 6-membered heterocyclic ring having one or more ring hetero atoms selected from the group consisting of oxygen, nitrogen and sulphur, that ring being optionally substituted by $C_1$-$C_8$-alkyl;
$R^9$ is hydrogen, $C_1$-$C_8$-alkyl optionally substituted by hydroxy, or $C_3$-$C_8$-cycloalkyl;
$R^{10}$ is $C_1$-$C_8$-alkyl;
$R^{11}$ is $C_1$-$C_8$-alkyl optionally substituted by halogen, hydroxy, $C_1$-$C_8$-alkoxy, cyano, amino, $C_1$-$C_8$-alkylamino or di($C_1$-$C_8$-alkyl)amino;
$R^{12}$ is hydrogen or $C_1$-$C_8$-alkyl;
$R^{13}$ is $C_1$-$C_8$-alkyl or $C_3$-$C_8$-cycloalkyl optionally substituted by hydroxy, amino, $C_1$-$C_8$-alkylamino or di($C_1$-$C_8$-alkyl)amino or $R^{12}$ and $R^{13}$ together with the nitrogen atom to which they are attached form a 5 or 6-membered saturated or unsaturated heterocyclic ring that contains one or more further hetero atoms selected from the group consisting of oxygen, nitrogen and sulphur, that ring being optionally substituted by $C_1$-$C_8$-alkyl; and
$R^{14}$ is $C_1$-$C_8$-alkyl optionally substituted by hydroxy or —$NR^{12}R^{13}$.

Terms used in the specification have the following meanings:

"Optionally substituted" as used herein means the group referred to can be substituted at one or more positions by any one or any combination of the radicals listed thereafter.

"$C_1$-$C_8$-alkyl" denotes straight chain or branched alkyl having 1 to 8 carbon atoms. Preferably, $C_1$-$C_8$-alkyl is $C_1$-$C_4$-alkyl.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl.

Preferably "$C_3$-$C_8$-cycloalkyl" is cyclopropyl, cyclobutyl, cyclopentyl, cyclohexyl, cycloheptyl or cyclooctyl.

"$C_1$-$C_8$-alkoxy" denotes straight chain or branched alkoxy having 1 to 8 carbon atoms. Preferably, $C_1$-$C_8$-alkoxy is $C_1$-$C_4$-alkoxy.

"Halogen" or "halo" may be fluorine, chlorine, bromine or iodine; preferably it is fluorine or chlorine.

"$C_1$-$C_8$-haloalkyl" denotes $C_1$-$C_8$-alkyl as hereinbefore defined substituted by one or more halogen atoms, preferably one, two or three halogen atoms, preferably fluorine or chlorine atoms. Preferably $C_1$-$C_8$-haloalkyl is $C_1$-$C_4$-alkyl substituted by one, two or three fluorine or chlorine atoms.

"$C_1$-$C_8$-alkylcarbonyl" denotes $C_1$-$C_8$-alkyl as hereinbefore defined attached by a carbon atom to a carbonyl group.

"$C_1$-$C_8$-alkylamino" and "di($C_1$-$C_8$-alkyl)amino" denote amino substituted respectively by one or two $C_1$-$C_8$-alkyl groups as hereinbefore defined, which may be the same or different. Preferably $C_1$-$C_8$-alkylamino and di($C_1$-$C_8$-alkyl)amino are respectively $C_1$-$C_4$-alkylamino and di($C_1$-$C_4$-alkyl)amino.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

$R^1$ may be, for example, pyrrole, pyrazole, imidazole, triazole, tetrazole, thiadiazole, oxazole, isoxazole, isothiazole, oxadiazole, pyridine, oxazole, pyrazine, pyridazine, pyrimidine, piperazine, morpholino, triazine, oxazine or thiazole. However $R^1$ is preferably an aromatic heterocyclic ring, especially pyrazine, pyridazine or pyrimidine. The heterocyclic ring may be substituted by one or more, e.g. one or two, specific optional halo, $C_1$-$C_8$-alkyl, $C_1$-$C_8$-alkoxy, $NR^6R^7$ substituents.

Where the heterocyclic ring is substituted by a further 5 or 6-membered heterocyclic ring this ring may be, for example, pyrrole, pyrazole, imidazole, triazole, tetrazole, oxazole, isoxazole, isothiazole, oxadiazole, pyridine, oxazole, pyrazine, pyridazine, pyrimidine, piperazine, morpholino, triazine, oxazine or thiazole, but it is preferably a saturated ring, especially piperazine or morpholino, optionally substituted by one or two $C_1$-$C_8$-alkyl groups.

Where $R^1$ is substituted by $C_1$-$C_8$-alkyl substituted by a 5 or 6-membered heterocyclic ring containing at least one ring hetero atom selected from the group consisting of nitrogen, oxygen and sulphur this ring may be, for example, pyrrole, pyrazole, imidazole, triazole, tetrazole, oxazole, isoxazole, isothiazole, oxadiazole, pyridine, oxazole, pyrazine, pyridazine, pyrimidine, piperazine, morpholino, triazine, oxazine or thiazole, but it is preferably morpholino or piperazine.

Where $R^4$ or $R^5$ is $C_1$-$C_8$-alkoxy substituted by a 5 or 6-membered heterocyclic ring containing at least one ring hetero atom selected from the group consisting of nitrogen, oxygen and sulphur this ring may be, for example, pyrrole, pyrazole, imidazole, triazole, tetrazole, oxazole, isoxazole, isothiazole, oxadiazole, pyridine, oxazole, pyrazine, pyridazine, pyrimidine, piperazine, morpholino, triazine, oxazine or thiazole, but it is preferably morpholino.

Where $R^4$ or $R^5$ is a 5 or 6-membered heterocyclic ring containing at least one ring hetero atom selected from the group consisting of nitrogen, oxygen and sulphur this ring may be, for example, pyrrole, pyrazole, imidazole, triazole, tetrazole, oxazole, isoxazole, isothiazole, oxadiazole, pyridine, oxazole, pyrazine, pyridazine, pyrimidine, piperazine, morpholino, triazine, oxazine or thiazole, but it is preferably imidazole or piperazine, and that ring is preferably substituted by $C_1$-$C_8$-alkyl, especially $C_1$-$C_4$-alkyl.

Preferred compounds of the present invention include compounds of formula I, in free or salt form, wherein $R^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_8$-alkyl optionally substituted by —$NR^6R^7$, carboxy, $C_1$-$C_8$-alkoxycarbonyl or a 5 or 6-membered heterocyclic ring containing at least one hetero atom selected from the group consisting of nitrogen, oxygen and sulphur, $C_1$-$C_8$-alkoxy, —$NR^6R^7$, $C_3$-$C_8$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_8$-alkyl;
$R^2$ is $C_1$-$C_8$-alkyl;
$R^3$ is $C_1$-$C_8$-alkoxy, $C_1$-$C_8$-alkylcarbonyl, —$SO_2NR^8R^9$, —$SOR^{10}$, —$SO_2R^{11}$ or carboxy and is in the para or meta position with respect to the indicated thiazole ring;
$R^4$ is hydrogen, $C_1$-$C_8$-alkoxy optionally substituted by a 5 or 6-membered heterocyclic ring containing at least one hetero atom selected from the group consisting of nitrogen, oxygen and sulphur, halo, halo-$C_1$-$C_8$-alkyl, —$SO_2NH_2$, —$NR^{12}R^{13}$ or a 5 or 6-membered heterocyclic ring containing at least one hetero atom selected from the group consisting of nitrogen, oxygen and sulphur, that ring being optionally substituted by $C_1$-$C_8$-alkyl;
$R^5$ is hydrogen;
$R^6$ is hydrogen or $C_1$-$C_8$-alkyl;
$R^7$ is $C_1$-$C_8$-alkyl optionally substituted by hydroxy, di($C_1$-$C_8$-alkyl)amino or a 5 or 6-membered heterocyclic ring containing at least one hetero atom selected from the group consisting of nitrogen and oxygen, that ring being optionally substituted by $C_1$-$C_8$-alkyl;
$R^8$ is hydrogen or $C_1$-$C_8$-alkyl optionally substituted by di($C_1$-$C_8$-alkyl)amino;
$R^9$ is hydrogen, $C_1$-$C_8$-alkyl optionally substituted by hydroxy, or $C_3$-$C_8$-cycloalkyl;
$R^{10}$ is $C_1$-$C_8$-alkyl;
$R^{11}$ is $C_1$-$C_8$-alkyl;
$R^{12}$ is $C_1$-$C_8$-alkyl; and
$R^{13}$ is $C_1$-$C_8$-alkyl optionally substituted by di($C_1$-$C_8$-alkyl)amino.

Further preferred compounds of formula I include those, in free or salt form, wherein $R^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_4$-alkyl optionally substituted by —$NR^6R^7$, carboxy, $C_1$-$C_4$-alkoxycarbonyl or a 5 or 6-membered heterocyclic ring containing at least one hetero atom selected from the group consisting of nitrogen, oxygen and sulphur, $C_1$-$C_4$-alkoxy, —$NR^6R^7$, $C_3$-$C_6$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_4$-alkyl;
$R^2$ is $C_1$-$C_4$-alkyl;
$R^3$ is $C_1$-$C_4$-alkoxy, $C_1$-$C_4$-alkylcarbonyl, —$SO_2NR^8R^9$, —$SOR^{10}$, —$SO_2R^{11}$ or carboxy and is in the para or meta position with respect to the indicated thiazole ring;
$R^4$ is hydrogen, $C_1$-$C_4$-alkoxy optionally substituted by a 5 or 6-membered heterocyclic ring containing at least one hetero atom selected from the group consisting of nitrogen, oxygen and sulphur, halo, halo-$C_1$-$C_4$-alkyl, —$SO_2NH_2$, —$NR^{12}R^{13}$ or a 5 or 6-membered heterocyclic ring containing at least one hetero atom selected from the group consisting of nitrogen, oxygen and sulphur, that ring being optionally substituted by $C_1$-$C_4$-alkyl;
$R^5$ is hydrogen;
$R^6$ is hydrogen or $C_1$-$C_4$-alkyl;
$R^7$ is $C_1$-$C_4$-alkyl optionally substituted by hydroxy, di($C_1$-$C_4$-alkyl)amino or a 5 or 6-membered heterocyclic ring containing at least one hetero atom selected from the group consisting of nitrogen and oxygen, that ring being optionally substituted by $C_1$-$C_4$-alkyl;
$R^8$ is hydrogen or $C_1$-$C_4$-alkyl optionally substituted by di($C_1$-$C_4$-alkyl)amino;
$R^9$ is hydrogen, $C_1$-$C_4$-alkyl optionally substituted by hydroxy, or $C_3$-$C_5$-cycloalkyl;
$R^{10}$ is $C_1$-$C_4$-alkyl;
$R^{11}$ is $C_1$-$C_4$-alkyl;
$R^{12}$ is $C_1$-$C_4$-alkyl; and
$R^{13}$ is $C_1$-$C_4$-alkyl optionally substituted by di($C_1$-$C_4$-alkyl)amino.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid.

These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

Specific preferred compounds of formula I are described hereinafter in the Examples.

The invention provides, in another aspect, a process for preparing a compound of formula I in free or salt form which comprises the steps of:

(i) (A) reacting a compound of formula II

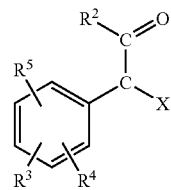

wherein $R^2$, $R^3$, $R^4$ and $R^5$ are as hereinbefore defined and X is halogen, with a compound of formula III

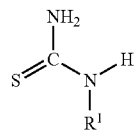

wherein $R^1$ is as hereinbefore defined;

(B) reacting a compound of formula IV

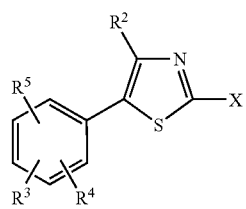

wherein $R^2$, $R^3$, $R^4$ and $R^5$ are as hereinbefore defined and X is halogen, with a compound of formula $R^1$—$NH^2$, optionally in the presence of a base;

(C) for the preparation of compounds of formula I where $R^1$ is a 5 or 6-membered heterocyclic ring containing nitrogen and optionally a further hetero atom of the group consisting of nitrogen, oxygen and sulphur that is substituted by —$NR^6R^7$, reacting a compound of formula I where $R^1$ is a 5 or 6-membered heterocyclic ring containing nitrogen and optionally a further hetero atom of the group consisting of nitrogen, oxygen and sulphur that is substituted by halo with a compound of formula V

wherein $R^6$ and $R^7$ are as hereinbefore defined, optionally in the presence of a base;

(D) for the preparation of compounds of formula I where $R^3$ is —$SO_2NR^8R^9$, reacting a compound of formula VI

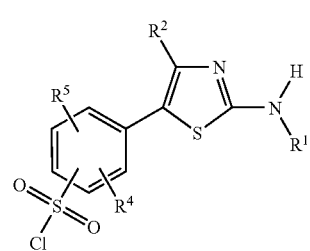

wherein $R^2$, $R^4$, $R^5$ and X are as hereinbefore defined with an amine of formula VII

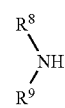

wherein $R^8$ and $R^9$ are as hereinbefore defined;

(E) for the preparation of compounds of formula I where one or both of $R^4$ and $R^5$ is —$NR^{12}R^{13}$, reacting a compound of formula I wherein $R^1$ and $R^2$ are hereinbefore defined, $R^3$ is —$SO_2R^{11}$ or —$SO_2NH_2$ and one or both of $R^4$ and $R^5$ is halo with a compound of formula VIII

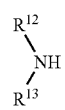

wherein $R^{12}$ and $R^{13}$ are hereinbefore defined, optionally in the presence of a base; or (F) for the preparation of compounds of formula I where one or both of $R^4$ and $R^5$ is $C_1$-$C_8$-alkoxy substituted by a 5 or 6-membered heterocyclic ring containing at least one hetero atom selected from the group consisting of nitrogen, oxygen and sulphur, reacting a compound of formula I wherein $R^1$ and $R^2$ are hereinbefore defined, $R^3$ is —$SO_2R^{11}$ or —$SO_2NH_2$ and one or both of $R^4$ and $R^5$ is halo with a compound of formula $HO$—$C_1$-$C_8$-alkyl-W where W is a 5 or 6-membered heterocyclic ring containing at least one hetero atom selected from the group consisting of nitrogen, oxygen and sulphur, optionally in the presence of a base; and (ii) recovering the resultant compound of formula I in free or salt form.

Process variant (A) may be carried out using known procedures for preparing aminothiazoles, or analogously, e.g. as hereinafter described in the Examples. The halogen X is preferably bromine or iodine. The reaction may be carried out in an organic solvent, e.g. an alcohol, such as ethanol, or pyridine. When the halogen is iodine and the solvent is pyridine the compounds of formula II are formed in situ. The reaction temperature may be from room temperature to the reflux temperature of the solvent, but conveniently from about 40 to 60° C. to the reflux temperature of the solvent.

Process variant (B) may be carried out using known procedures for reaction of hetero aryl halides with primary or secondary amines, or analogously, e.g. as hereinafter described in the Examples. The halogen X is preferably chlorine or bromine. The reaction may be carried out in an organic solvent, e.g. dimethylacetamide or dimethylsulfoxide, and when it is carried out in the presence of an alkali metal salt that alkali metal salt is preferably caesium carbonate. The reaction temperature may be from room temperature to the reflux temperature of the solvent, but conveniently about 110 to 130° C.

Process variant (C) may be carried out using known procedures for reaction of heteroaryl halides with primary or secondary amines, or analogously, e.g. as hereinafter described in the Examples. It may be carried out neat but when it is carried out in the presence of an alkali metal salt that salt is preferably caesium carbonate. The reaction temperature may be from 50 to 200° C., but conveniently about 90 to 110° C.

Process variant (D) may be carried out using known procedures for reacting sulfonyl chlorides with amines, or analogously, e.g. as hereinafter described in the Examples. The reaction may be carried out in an organic solvent, e.g. dioxane. The reaction temperature may be from room temperature to the reflux temperature of the solvent, but conveniently room temperature.

Process variant (E) may be carried out using known procedures for reacting aryl halides with amines. The reaction may be carried out in an organic solvent, for example dimethylformamide (DMF) but preferably dimethylsulfoxide (DMSO), preferably in the presence of a base, which is preferably caesium carbonate. The reaction temperature is conveniently 100 to 150° C.

Process variant (F) may be carried out using known procedures for reacting aryl halides with alcohols. The reaction may be carried out in an organic solvent, for example dimethylformamide (DMF) but preferably dimethylsulfoxide (DMSO), preferably in the presence of a base, which is preferably caesium carbonate. The reaction temperature is conveniently 100 to 150° C.

Compounds of formula II may be prepared by reacting a compound of formula IX

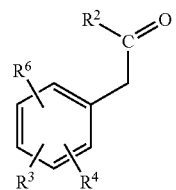

IX wherein $R^2$, $R^3$, $R^4$ and $R^5$ are as hereinbefore defined, with a halogen, preferably bromine or iodine, using known procedures for the alpha halogenation of ketones.

Compounds of formula III may be prepared by known methods, for example by reacting a compound of formula $R^1$—$NH_2$, where $R^1$ is as hereinbefore defined, with benzoyl isothiocyanate and hydrolysing the resulting product, for example to replace the benzoyl group by hydrogen, e.g. as hereinafter described in the Examples. The reaction with benzoyl isothiocyanate may be carried out in an organic solvent, for example an alcohol such as ethanol. Suitable reaction temperatures are from room temperature to reflux temperature of the solvent, conveniently 35-45° C. The hydrolysis may be effected at elevated temperature, for example 60 to 80° C. to reflux temperature, conveniently at reflux temperature.

Compounds of formula IV may be prepared from aminothiazole compounds by known reactions for conversion of aryl or heteroaryl amines to aryl or heteroaryl halides, for example by diazotization of the heteroaryl amine followed by addition of the diazonium salt to the copper(II) halide in an aqueous solution with the corresponding halogeno acid (Sandmeyer Reaction) or by treatment of the heteroaryl amine with an alkyl nitrite in the presence of anhydrous copper (U) salts as described in M. P. Doyle, B. Siegfried, J. F. Dellaria, Jr., *Journal of Organic Chemistry*, 42, 1977, p 2426. Compounds of formula V are either commercially available or may be prepared by known methods.

Compounds of formula VI may be prepared from compounds of formula I wherein $R^3$ is nitro by known reactions for converting aryl nitro-substituted compounds to their corresponding aryl sulfonyl chlorides, for example by firstly hydrogenating to the aniline, e.g. using hydrogen in the presence of 10% Palladium on carbon, then secondly reacting with nitrous acid to give the diazo compound and finally reacting with $SO_2$/acetic acid/$CuCl_2H_2O$. The first step may be carried out in an organic solvent, for example a mixture of ethyl acetate and tetrahydrofuran. Suitable reaction temperatures are from room temperature to reflux temperature of the solvent, but conveniently room temperature.

Compounds of formula VII are either commercially available or may be prepared by known methods.

Compounds of formula VIII are either commercially available or may be prepared by known methods.

Compounds of formula IX where $R^3$ is —$SO_2NR^8R^9$ may be prepared as described in EP 91749 A2.

Compounds of formula IX where $R^3$ is —$SO_2NR^8R^9$ may be prepared by reacting a compound of formula IX where $R^3$ is hydrogen and $R^4$ is —$C_1$-$C_8$-alkoxy or chlorine, with chlorosulfonic acid, followed by treatment with an amine or ammonia as described in the Examples.

Compounds of formula IX where $R^3$ is —$SO_2NR^8R^9$ may also be prepared from the compound of formula IX where $R^3$ is —$NH_2$, $R^4$ and $R^5$ being hydrogen, by reaction with nitrous acid to give a diazo compound which is then reacted with sulphur dioxide in the presence of copper chloride, for example by the method described in E. E. Gilbert, *Synthesis* 1969, 1-10, to give the corresponding sulfonyl chloride of formula IX where $R^3$ is meta $SO_2Cl$, $R^4$ and $R^5$ being hydrogen. This is then treated with ammonia or an amine as described in the Examples.

Compounds of formula IX where $R^3$ is —$NH_2$, $R^2$ is methyl and $R^4$ and $R^5$ are hydrogen, may be prepared from the compound of formula IX where $R^3$ is —$NO_2$, $R^4$ and $R^5$ being hydrogen, by hydrogenation, e.g. using hydrogen in the presence of 10% palladium on carbon, in an organic solvent, for example a mixture of ethyl acetate and tetrahydrofuran (THF).

Compounds of formula IX where $R^3$ is —$SO_2R^{11}$, $R^4$ is -fluoride or -trifluoromethyl and $R^5$ is hydrogen may be prepared from compounds of formula X where $R^4$ is F or $CF_3$ by known methods, for example as described in R. V. Heinzelman, *Org. Synth.*, 1963, IV, 573.

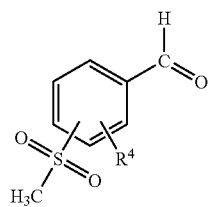

X

The compound of formula X where $R^4$ is chlorine may be prepared as described in international patent application WO 01/49660 A1.

Compounds of formula X where $R^4$ is fluorine or trifluoromethyl may be prepared from commercially available compounds of formula XI where $R^4$ is fluorine or trifluoromethyl by reaction with the sodium salt of methane sulfinic acid in an organic solvent, for example dimethylsulfoxide (DMSO). The reaction temperature may be from room temperature to 100° C. but conveniently about 70° C.

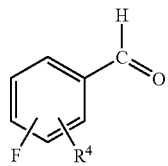

XI

Compounds of formula XI are either commercially available or may be prepared by known methods.

Compounds of formula I and their pharmaceutically acceptable salts are useful as pharmaceuticals. In particular, they exhibit inhibition of phosphatidylinositol 3-kinase (Pi3 kinase) enzymes, especially the gamma isoform (p110γ), which are responsible for generating phosphorylated signalling products. The inhibitory properties of compounds of formula I may be demonstrated in the following test procedures:

Baculovirus expressing different fragments of human PI3Kγ fused to glutathione S-transferase (GST) have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.*, 324:489. Residues 38-1102 of human PI3Kγ are subcloned into the BamH1 and EcoR1 sites of the transfer vector pAcG2T (Pharmingen) to create a GST-PI3Kγ lacking the first 37 residues of PI3Kγ. To express the recombinant protein, Sf9 (*Spodoptera frugiperda* 9) insect cells are routinely maintained at densities between $3 \times 10^5$ and $3 \times 10^6$ cells/ml in serum containing TNMPH medium (Sigma). Sf9 cells, at a density of $2 \times 10^6$ are infected with human GST-PI3KγΔ34 baculovirus at a multiplicity of infection (m.o.i.) of 1 for 72 hours. The infected cells are harvested by centrifugation at 1400 g for 4 minutes at 4° C. and the cell pellets are frozen at –80° C. Both Sf9 and Sf21 cells work equally well. Sf9 cells ($1 \times 10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at –20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 μl test compound in 5% dimethylsulphoxide and 20 μl assay mix (40 mM Tris, 200 mM NaCl, 2 mM ethyleneglycol-aminoethyl-tetraacetic acid (EGTA), 15 μg/ml phosphatidylinositol, 12.5 μM adenosine triphosphate (ATP), 25 mM $MgCl_2$, 0.1 μCi [$^{33}$P]ATP). The reaction is started by the addition of 20 μl of enzyme mix (40 mM Tris, 200 mM NaCl, 2 mM EGTA containing recombinant GST-p110γ). The plate is incubated at room temperature for 60 minutes and the reaction terminated by the adding 150 μl of WGA-bead stop solution (40 mM Tris, 200 mM NaCl, 2 mM EGTA, 1.3 mM ethylene diamine tetraacetic acid (EDTA), 2.6 μM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 μl of 5% dimethylsulphoxide (DMSO) and non-specific activity is determined by adding 10 μl 50 mM EDTA in place of the test compound.

Compounds of the Examples hereinbelow have $IC_{50}$ values below 0.60 μM in the aforementioned assay.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siaerosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone dipropionate, fluticasone propionate, ciclesonide or mometasone furoate and compounds described in WO 0200679, WO 0288167, WO 0212266 and WO 02100879, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)-propyl]-sulfonyl]ethyl]-amino]ethyl]-2(3H)-benzothiazolone and pharmaceutically acceptable salts thereof (the hydrochloride being Viozan®—AstraZeneca), and PDE4 inhibitors such as Ariflo® (GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) as well as those described in WO 98/18796 and WO 03/39544. Such bronchodilatory drugs include anti-cholinergic or antimuscarinic agents, in particular ipratropium bromide, oxitropium bromide and tiotropium salts but also those described in WO 01/04118, WO 02/51841, WO 02/53564, WO 03/00840, WO 03/87094, WO 04/05285, WO 02/00652, WO 03153966, EP 424021, U.S. Pat. No. 5,171,744, U.S. Pat. No. 3,714,357 and WO 03/33495, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially a compound of formula

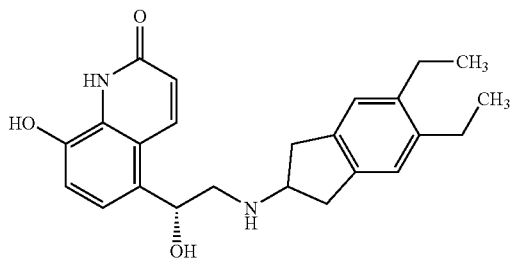

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahy-dro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules.

Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

Dosages of agents of the invention employed in practicing the present invention will of course vary depending, for example, on the particular condition to be treated, the effect desired and the mode of administration. In general, suitable daily dosages for oral administration are of the order of 0.1 to 10 mg/kg.

EXAMPLES

Compounds of formula I which are also of formula XII

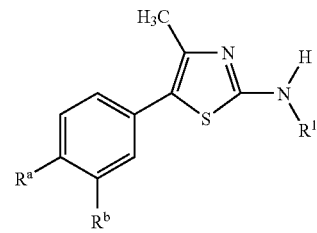

XII are shown in Table I below, the method of preparation being described hereinafter. The table also shows mass spectrometry data. The Examples are in free form.

TABLE 1

| Ex. | R$^a$ | R$^b$ | R$^1$ | M/s MH+ |
|---|---|---|---|---|
| 1 | —SO$_2$NH$_2$ | H | 5-methylpyrazin-2-yl | 347.9 |
| 2 | —SO$_2$NH$_2$ | H | 6-chloro-3-methylpyrazin-2-yl | 381.9 |
| 3 | —SO$_2$NH$_2$ | H | 6-methoxy-3-methylpyrazin-2-yl | 378.1 |
| 4 | —SO$_2$NH$_2$ | H | 6-methylpyridin-2-yl | 347.0 |
| 5 | —SO$_2$NH$_2$ | H | 5-chloro-6-methylpyridin-2-yl | 381.1 |
| 6 | —SO$_2$NH$_2$ | H | 6-ethoxy-3-methylpyridin-2-yl | 390.9 |
| 7 | —SO$_2$NH$_2$ | H | 5-methylpyridin-3-yl | 347.0 |
| 8 | —SO$_2$NH$_2$ | H | 6-methoxy-3-methylpyridin-2-yl | 376.9 |
| 9 | —SO$_2$NH$_2$ | H | 4-methylpyridin-3-yl | 347.0 |
| 10 | —SO$_2$NH$_2$ | H | 2-methylpyrimidin-4-yl | 348.1 |
| 11 | —SO$_2$NH$_2$ | H | 6-methoxy-4-methylpyrimidin-5-yl | 378.0 |

TABLE 1-continued
| Ex. | R$^a$ | R$^b$ | R$^1$ | M/s MH+ |
|---|---|---|---|---|
| 12 | —SO$_2$NH$_2$ | H | 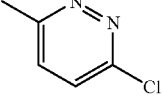 | 382.0 |
| 13 | —SO$_2$NH$_2$ | H | 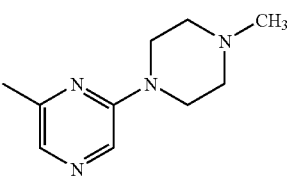 | 446.2 |
| 14 | —SO$_2$NH$_2$ | H | 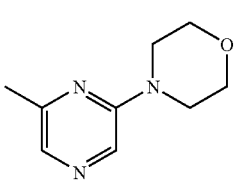 | 433.2 |
| 15 | —SO$_2$NH$_2$ | H | 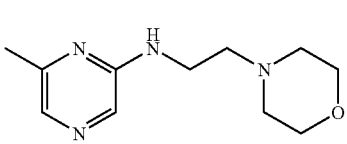 | 475.9 |
| 16 | —SO$_2$NH$_2$ | H | 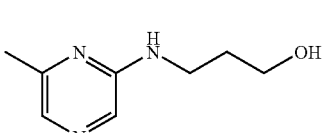 | 421.2 |
| 17 | —SO$_2$NH$_2$ | H | 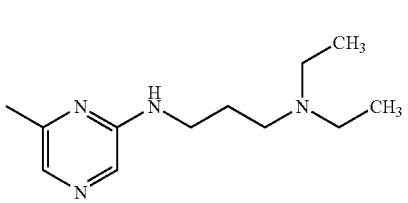 | 476.0 |
| 18 | 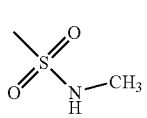 | H | 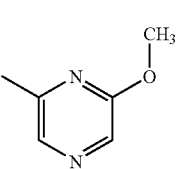 | 392.2 |
| 19 | 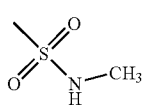 | H | 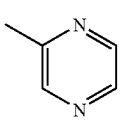 | 362.2 |
| 20 | 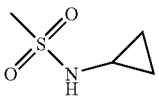 | H | 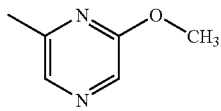 | 418.2 |
| 21 | 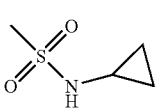 | H | 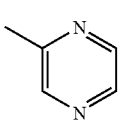 | 388.2 |

TABLE 1-continued

| Ex. | $R^a$ | $R^b$ | $R^1$ | M/s MH+ |
|---|---|---|---|---|
| 22 | —OCH₃ | —SO₂NH₂ | 5-methylpyrazin-2-yl | 378.2 |
| 23 | —SO₂NH₂ | Cl | 5-methylpyrazin-2-yl | 381.9 |
| 24 | —SO₂NH₂ | Cl | 5-methylpyridin-3-yl | 380.9 |
| 25 | —SO₂NH₂ | H | 5-methyl-1,3,4-thiadiazol-2-yl | 367.9 |
| 26 | —SO₂NH₂ | H | 3-methyl-1H-1,2,4-triazol-5-yl | 336.9 |
| 27 | —S(O)CH₃ | H | 5-methylpyrazin-2-yl | 330.9 |
| 28 | —S(O)₂CH₃ | H | 5-methylpyrazin-2-yl | 346.99 |
| 29 | —S(O)₂CH₃ | H | 3-chloro-6-methylpyrazin-2-yl | 380.8 |
| 30 | —S(O)₂CH₃ | Cl | 5-methylpyridin-3-yl | 379.99 |
| 31 | —S(O)₂CH₃ | H | 5-methyl-6-(4-methylpiperazin-1-yl)pyridin-2-yl | 443.8 |

Preparation of Specific Examples

Example 1

4-[4-Methyl-2-(pyrazin-2-ylamino)-thiazol-5-yl]-benzenesulfonamide

1a) Pyrazin-2-yl-thiourea

Aminopyrazine (2 g, 21.03 mmol) is dissolved in ethanol (20 ml) and benzoylisothiocyanate (2.82 ml) is added dropwise. The mixture is heated to 80° C. with stirring for 10 minutes then allowed to cool to room temperature. The solvent is removed in vacuo and the resulting solid dissolved in 1M sodium hydroxide (30 ml) and heated under reflux for 1 hour. The resultant suspension is filtered and the solid washed with water and a little cold methanol. The solid is dried in vacuo to yield the title compound, m.p. 239-239.5° C., MH+ (AP+): 138 (M+-NH₃).

Other thioureas used are either commercially available or prepared in an analogous manner from the appropriate starting amine.

1b) 4-[4-Methyl-2-(pyrazin-2-ylamino)-thiazol-5-yl]-benzenesulfonamide

Bromine (0.017 ml, 0.33 mmol) is added dropwise to a stirred solution of 4-(2-oxo-propyl)-benzenesulfonamide (prepared as described in European patent specification EP 91749 A2) (0.087 g, 4.1 mmol) in dioxan (10 ml) at 0° C. After 30 minutes the solvent is removed and the crude product is dissolved in ethanol (4.0 ml). Pyrazin-2-yl-thiourea (0.063 g, 0.41 mmol) is added and the stirred reaction mixture is heated at 60° C. for 3 hours. The solvent is removed and the residue is triturated with ethyl acetate to give the title compound as a pale orange solid (0.040 g). MH$^+$ (AP+):

Example 2

4-[2-(6-Chloro-pyrazin-2-ylamino)-4-methyl-thiazol-5-yl]-benzenesulfonamide 4-(2-Oxo-propyl)-benzenesulfonamide (prepared as described in European patent specification EP 91749 A2) (0.63 g, 2.9 mmol) is dissolved in dry dioxan (70 ml) at 0° C. and bromine (0.121 ml, 2.4 mmol) is added dropwise. The mixture is stirred for 45 minutes at room temperature then the solvent is removed in vacuo. 6-Chloro-pyrazin-2-yl-thiourea (0.35 g, 1.87 mmol) is added to a solution of the above bromide (0.546 g, 1.87 mmol) in ethanol and the solution is heated at 60° C. for 4 hours. The reaction mixture is allowed to cool and the solvent removed under vacuum to give the title compound (0.63 g). MH$^+$ (ES+): 382.1, 384.2 (3:1)

Examples 3 to 12

These compounds, namely
4-[2-(6-methoxy-pyrazin-2-ylamino)-4-methyl-thiazol-5-yl]-benzenesulfonamide,
4-[4-methyl-2-(pyridin-2-ylamino)-thiazol-5-yl]-benzenesulfonamide,
4-[2-(5-chloro-pyridin-2-ylamino)-4-methyl-thiazol-5-yl]-benzenesulfonamide,
4-[2-(6-ethoxy-pyridin-2-ylamino)-4-methyl-thiazol-5-yl]-benzenesulfonamide,
4-[4-methyl-2-(pyridin-3-ylamino)-thiazol-5-yl]-benzenesulfonamide,
4-[2-(6-methoxy-pyridin-3-ylamino)-4-methyl-thiazol-5-yl]-benzenesulfonamide,
4-[4-methyl-2-(pyridin-4-ylamino)-thiazol-5-yl]-benzenesulfonamide,
4-[4-methyl-2-(pyrimidin-2-ylamino)-thiazol-5-yl]-benzenesulfonamide,
4-[2-(6-methoxy-pyrimidin-4-ylamino)-4-methyl-thiazol-5-yl]-benzenesulfonamide and
4-[2-(6-chloro-pyridazin-3-ylamino)-4-methyl-thiazol-5-yl]-benzenesulfonamide
respectively, are prepared by the procedure of Example 2 from 4-(2-oxo-propyl)-benzenesulfonamide (prepared as described in European patent specification EP 91749 A2) and the appropriate thiourea.

Example 13

4-[4-Methyl-2-(4-methyl-3,4,5,6-tetrahydro-2.H.-[1,2]bipyrazinyl-6'-ylamino)-thiazol-5-yl]-benzenesulfonamide 4-[2-(6-Chloro-pyrazin-2-ylamino)-4-methyl-thiazol-5-yl]-benzenesulfonamide (2) (50 mg, 0.13 mmol) and 1-methylpiperazine (0.147 ml, 1.31 mmol) are heated, with stirring under argon, at 80° C. for 18 hours. The reaction mixture is azeotroped with toluene (2×20 ml) then dissolved in ethyl acetate and washed with water (50 ml) followed by brine (50 ml). After drying (MgSO$_4$) the mixture is filtered and the solvent is removed to give a brown solid. Addition of CH$_2$Cl$_2$ affords the title compound (0.013 g).

Examples 14 to 17

These compounds, namely 4-[4-methyl-2-(6-morpholin-4-yl-pyrazin-2-ylamino)-thiazol-5-yl]-benzenesulfonamide, 4-{4-methyl-2-[6-(2-morpholin-4-yl-ethylamino)-pyrazin-2-ylamino]-thiazol-5-yl}-benzenesulfonamide, 4-{2-[6-(3-hydroxy-propylamino)-pyrazin-2-ylamino]-4-methyl-thiazol-2-yl}-benzenesulfonamide and 4-{2[6-(3-diethylamino-propylamino)-pyrazin-2-ylamino]-4-methyl-thiazol-5-yl}-benzenesulfonamide respectively, are prepared from 4-[2-(6-chloro-pyrazin-2-ylamino)-4-methyl-thiazol-5-yl]-benzenesulfonamide (Example 2) and the appropriate amine following the procedure of Example 11.

Example 18

4-[2-(6-Methoxy-pyrazin-2-ylamino)-4-methyl-thiazol-5-yl]-N-methyl-benzene-sulfonamide 18a)
N-Methyl-4-(2-oxo-propyl)-benzenesulfonamide 4-(2-Oxo-propyl)-benzenesulfonyl chloride (prepared as described in European patent specification EP 91749 A2) (0.087 g, 4.1 mmol) was treated with methylamine to give the title compound.

18b) 4-[2-(6-Methoxy-pyrazin-2-ylamino)-4-methyl-thiazol-5-yl]-N-methyl-benzene-sulfonamide Using N-methyl-4-(2-oxo-propyl)-benzenesulfonamide (18a) and (6-methoxy-pyrazin-2-yl)-thiourea in an identical process to that described for the preparation of 4-[4-methyl-2-(pyrazin-2-ylamino)-thiazol-5-yl]-benzenesulfonamide (Example 1) afforded the title compound.

Examples 19 to 21

These compounds, namely N-methyl-4-[4-methyl-2-(pyrazin-2-ylamino)-thiazol-5-yl]-benzenesulfonamide, N-cyclopropyl-4-[2-(6-methoxy-pyrazin-2-ylamino)-4-methyl-thiazol-5-yl]-benzenesulfonamide and N-cyclopropyl-4-[4-methyl-2-(pyrazin-2-ylamino)-thiazol-5-yl]-benzenesulfonamide respectively, are prepared by analogous procedures to those used for 4-[2-(6-methoxy-pyrazin-2-ylamino)-4-methyl-thiazol-5-yl]-N-methyl-benzenesulfonamide (Example 16), starting from 4-(2-oxo-propyl)-benzenesulfonyl chloride (prepared as described in European patent specification EP 91749 A2) and using the appropriate amine and thiourea.

Example 22

2-Methoxy-5-[4-methyl-2-(pyrazin-2-ylamino)-thiazol-5-yl]-benzenesulfonamide

2-Methoxy-5-(2-oxo-propyl)-benzenesulfonamide (S. Sakurai et al. Chem. Pharm. Bull. 40(6) 1443-1451 (1992)) (0.3 g, 1.23 mmol), pyrazin-2-yl-thiourea (0.19 g, 1.23 mmol), iodine (0.31 g, 1.23 mmol) in pyridine (2.5 ml) is stirred at 60° C. for 20 hours. The mixture is concentrated. To the residue is added water, the precipitate is collected and recrystallised from ethanol to give the titled compound (0.103 g). m.p. 378.2° C.

Example 23

2-Chloro-4-[4-methyl-2-pyrazin-2-ylamino)-thiazol-5-yl]-benzenesulfonamide 23a) 1-(4-Amino-3-chloro-phenyl)-propan-2-one N-Chlorosuccinamide (1.79 g, 13.4 mmol) is added to a stirred solution of 1-(4-amino-phenyl)-propan-2-one (2.0 g, 13.4 mmol) in chloroform at 0° C. After 1 hour the reaction is complete. The solvent is removed to give the title compound.

23b) 2-Chloro-4-(2-oxo-propyl)-benzenesulfonyl chloride

Concentrated hydrochloric acid (4 ml) is added slowly to a stirred solution of 1-(4-Amino-3-chloro-phenyl)-propan-2-one (23a) (2.4 g, 13.1 mmol) in acetic acid (80 ml) at 0° C. A solution of sodium nitrite (0.90 g, 13.1 mmol) in water (4.0 ml) is added dropwise. After 20 minutes a solution of the above reagent ($SO_2$/AcOH/$CuCl_2$/$H_2O$) (100 ml) at 0° C. is added and the mixture is allowed to warm to room temperature and stirred for 1 hour. The mixture is diluted with water (100 ml) and extracted with dichloromethane (3×100 ml). The organic extracts are combined, washed with brine (100 ml), dried ($MgSO_4$), filtered and the solvent is removed to afford the title compound (3.5 g) which is used crude in the subsequent reaction.
Preparation of the Reagent $SO_2$/AcOH/$CuCl_2$/$H_2O$:

In accordance with the method described in E. E. Gilbert, Synthesis 1969, 1-10, p6, glacial acetic acid (100 ml) vigorously stirred at room temperature is treated by bubbling $SO_2$ gas. Once a saturated solution is achieved (approximately 10 g per 100 ml), the solution is treated with copper (II) chloride (4 g) in water (5 ml). The resulting mixture is allowed to settle to give a green solution.

23c) 2-Chloro-4-(2-oxo-propyl)-benzenesulfonamide

Aqueous ammonia solution (5 ml) is added to a stirred solution of the crude sulfonyl chloride (23b) (0.70 g, 2.62 mmol) in tetrahydrofuran (100 ml) at 0° C. After 2 hours the reaction mixture is concentrated in vacuo. The residue is diluted with water (100 ml) and extracted with ethyl acetate (100 ml). The organic extract is dried ($MgSO_4$) and the solvent removed to give an oil. Purification by chromatography on silica, eluting with ethyl acetate, affords the title compound (0.154 g).

23d) 4-(1-Bromo-2-oxo-propyl)-2-chloro-benzene-sulfonamide

Bromine 0.022 ml, 0.42 mmol) is added to a stirred solution of ketone (23c) (0.15 g, 6.1 mmol) in dioxan (15 ml). After 30 minutes the solvent is removed to give a brown oil (0.2 g).

23e) 2-Chloro-4-[4-methyl-2-(pyrazin-2-ylamino)-thiazol-5-yl]-benzenesulfonamide Pyrazin-2-yl-thiourea (Example 1a) (0.047 g, 0.31 mmol) is added to a stirred solution of 4-(1-bromo-2-oxo-propyl)-2-chloro-benzenesulfonamide (0.10 g, 0.31 mmol) in ethanol (5 ml). The solution is heated at 60° C. for 3 hours. The mixture is filtered to remove the precipitate which is washed with methanol and dried. (0.055 g).

Example 24

2-Chloro-4-[4-methyl-2-(pyridin-3-ylamino)-thiazol-5-yl]-benzenesulfonamide

3-Pyridylthiourea (0.047 g, 0.31 mmol) is added to a stirred solution of 4-(1-Bromo-2-oxo-propyl)-2-chloro-benzene-sulfonamide (Example 23d) (0.10 g, 0.31 mmol) in ethanol (5 ml). The solution is heated at 60° C. for 3 hours. The solvent is removed and the residue is purified by chromatography on silica eluting with ethyl acetate-hexane to give the title compound (0.020 g).

Example 25

4-[4-Methyl-2-([1,3,4]thiadiazol-2-ylamino)-thiazol-5-yl]-benzenesulfonamide 25a) 4-Methyl-5-(4-nitro-phenyl)-thiazol-2-ylamine A solution of N-[4-methyl-5-(4-nitro-phenyl)-thiazol-2-yl]-acetamide (prepared by the method described in J. Liebscher, E. Mitzner, Synthesis, 1985, (4), p 414) (10 g, 36 mmol) in ethanol (200 ml) and 7M hydrochloric acid (50 ml) is heated at reflux with stirring for 4 hours. After standing at room temperature for 4 days the hydrochloride salt of the title compound (8.15 g) precipitates as yellow crystals which are removed by filtration and dried. The title compound (free base) is obtained by partitioning the hydrochloride salt between aqueous sodium hydroxide and ethyl acetate. The organic extract is separated, dried ($MgSO_4$) and the solvent is removed to give an orange solid (6.58 g). 1N nmr ($CDCl_3$): 2.38 (4H, s, Me), 5.02 (2H, br s, $NH_2$), 7.45 (2H, d), 8.20 (2H, d)

25b) 2-Chloro-4-methyl-5-(4-nitro-phenyl)-thiazole

Isoamyl nitrite (3.5 ml, 25 mmol) is added to a stirred suspension/solution of anhydrous copper (II) chloride (2.75 g, 20 mmol) in dry methylcyanide (50 ml). 4-Methyl-5-(4-nitro-phenyl)-thiazol-2-ylamine (25a) (4.0 g, 17 mmol) is then added over 30 minutes. The resulting slurry is stirred at room temperature for 1 hour then heated at 70° C. for 30 minutes. After cooling to room temperature the black solution is poured into 4M hydrochloric acid (200 ml). The product is extracted with ethyl acetate, dried ($MgSO_4$) and the solvent removed to give the title compound as an orange powder (3.13 g). $MH^+$ (TOF, ES+): 255.0

25c) 4-(2-Chloro-4-methyl-thiazol-5-yl)-phenylamine

Indium powder (0.64 mg, 2.5 mmol) and saturated ammonium chloride solution (3 ml, 2.5 mmol) are added to a solution of 2-chloro-4-methyl-5-(4-nitro-phenyl)-thiazole (25b) (0.20 g, 0.786 mmol) in ethanol (3 ml). The mixture is heated at reflux with stirring for 90 minutes. When cool the mixture is diluted with 2M aqueous hydrochloric acid to dissolve any product and the mixture is filtered through celite. The filtrate is adjusted to pH 9 with aqueous sodium hydroxide and extracted with dichloromethane (3×30 ml). The combined organic extract is dried (MgSO$_4$) filtered, and the solvent removed to give the title compound as a yellow solid (0.17 g).

25d) 4-(2-Chloro-4-methyl-thiazol-5-yl)-benzenesulfonamide

Starting from 4-(2-chloro-4-methyl-thiazol-5-yl)-phenylamine (25c) and following the two step process described for the preparation of 2-chloro-4-(2-oxo-propyl)-benzenesulfonamide (Example 23c) from 1-(4-amino-3-chloro-phenyl)-propan-2-one (Example 23a) gave the title compound.

25e) 4-[4-Methyl-2-([1,3,4]thiadiazol-2-ylamino)-thiazol-5-yl]-benzenesulfonamide Caesium carbonate (0.08 g, 0.24 mmol) and 5-methyl-[1,3,4]thiadiazol-2-ylamine (0.031 g, 0.27 mmol) are added to a solution of 4-(2-chloro-4-methyl-thiazol-5-yl)-benzenesulfonamide (25d) (0.07 g, 0.24 mmol) in dimethylacetamide (2 ml). The mixture is heated with stirring at 110° C. for 18 hours. After adding more 5-methyl-[1,3,4]thiadiazol-2-ylamine (0.056 g, 0.49 mmol) heating is continued at 130° C. for an additional 8 hours. The solvent is removed and the product is purified by chromatography on silica eluting with ethyl acetate to give an orange solid. Trituration with ethyl acetate-methanol affords the title compound as a yellow solid (0.0081 g)

Example 26

4-[4-Methyl-2-(1.H.-[1,2,4]triazol-3-ylamino)-thiazol-5-yl]-benzenesulfonamide Replacing 5-methyl-[1,3,4]thiadiazol-2-ylamine with 1.H.-[1,2,4]triazol-3-ylamine in the procedure described for preparing 4-[4-methyl-2-([1,3,4]thiadiazol-2-ylamino)-thiazol-5-yl]-benzenesulfonamide (Example 25e) from 4-(2-chloro-4-methyl-thiazol-5-yl)-benzenesulfonamide (Example 25d) affords the title compound.

Example 27

[5-(4-Methanesulfinyl-phenyl)-4-methyl-thiazol-2-yl]-pyrazin-2-yl-amine

27a) 1-Methylsulfanyl-4-(2-nitro-propenyl)-benzene

A stirred solution of 4-methylsulfanyl-benzaldehyde (5.0 g, 28.8 mmol) and ammonium acetate (0.666 g, 8.6 mmol) in nitroethane (17 ml, 236 mmol) is heated at reflux for 5 hours. The solvent is removed and the residue is dissolved in CHCl$_3$ (100 ml) and washed with water (100 ml) followed by brine (100 ml). After drying (MgSO$_4$) the solvent is removed to give the title compound as a yellow solid which is used crude in the next step.

27b) 1-(4-Methylsulfanyl-phenyl)-propan-2-one

A stirred mixture of crude 1-methylsulfanyl-4-(2-nitropropenyl)-benzene (27a) (28.8 mmol) iron filings (6.25 g, 112 mmol) and ferric chloride hexahydrate (0.155 g, 0.57 mmol) in water (20 ml) is heated to reflux. Concentrated hydrochloric acid (10 ml) is added over 2 hours the reflux continued for 4 hours. After 18 hours at room temperature the reaction is diluted with water and chloroform. The mixture is filtered through celite and the organic extract is separated. The aqueous extract is extracted with chloroform and the combined organic extracts are dried (MgSO$_4$). The solvent is removed and the residue is purified by chromatography on silica eluting with hexane-ethyl acetate (3:1) to afford the title compound (2.65 g).

27c) [4-Methyl-5-(4-methylsulfanyl-phenyl)-thiazol-2-yl]-pyrazin-2-yl-amine Using 1-(4-methylsulfanyl-phenyl)-propan-2-one (27b) and pyrazin-2-yl-thiourea (1a) in an analogous procedure described for the preparation of 4-[4-methyl-2-(pyrazin-2-ylamino)-thiazol-5-yl]-benzenesulfonamide (Example 1b) affords the title compound.

27d) [5-(4-Methanesulfinyl-phenyl)-4-methyl-thiazol-2-yl]-pyrazin-2-yl-amine Hydrogen peroxide solution (27% in water) (35 ml, 0.28 mmol) is added to a stirred suspension of [4-methyl-5-(4-methylsulfanyl-phenyl)-thiazol-2-yl]-pyrazin-2-yl-amine (27c) (0.090 g, 0.28 mmol) in acetic acid (5 ml). After 30 minutes the reaction is diluted with water and brought to pH 10 by addition of aqueous sodium hydroxide. The product is extracted with ethyl acetate (3×50 ml), the combined organic extracts are washed with brine (50 ml), dried (MgSO$_4$) and the solvent removed to give the title compound as an orange solid (0.03 g).

Example 28

[5-(4-Methanesulfonyl-phenyl)-4-methyl-thiazol-2-yl]-pyrazin-2-yl-amine

Oxone (Potassium peroxymonosulfate) (0.417 g, 0.77 mmol) is added to a stirred solution of [4-methyl-5-(4-methylsulfanyl-phenyl)-thiazol-2-yl]-pyrazin-2-yl-amine (27c) (0.05 g, 0.16 mmol) in acetone-water (9:1). After 2 hours at room temperature the solid precipitate is removed by filtration. The solid is dissolved in methanol, filtered to remove oxone and the solvent is removed from the filtrate to afford the title compound as a yellow solid (0.022 g).

Example 29

(6-Chloro-pyrazin-2-yl)-[5-(4-methanesulfonyl-phenyl)-4-methyl-thiazol-2-yl]-amine The title compound is prepared following the same route as Example 28, replacing 6-pyrazin-2-yl-thiourea with 6-chloro-pyrazin-2-yl-thiourea.

Example 30

[5-(3-Chloro-4-methanesulfonyl-phenyl)-4-methyl-thiazol-2-yl]-pyridin-3-yl-amine The title compound is prepared starting from 3-chloro-4-methanesulfonyl-benzaldehyde (prepared as described in WO 01/49660 A1) and 3-pyridylthiourea following an analogous sequence of reactions described for the preparation of [4-Methyl-5-(4-methylsulfanyl-phenyl)-thiazol-2-yl]-pyrazin-2-yl-amine (27c) from 4-methylsulfanyl-benzaldehyde.

Example 31

[5-(4-Methanesulfonyl-phenyl)-4-methyl-thiazol-2-yl]-[6-(4-methyl-piperazin-1-yl)-pyridin-3-yl]-amine

31a) 4-Methanesulfonyl-benzaldehyde

4-Chlorobenzaldehyde (5.0 g, 36 mmol) and methanesulfinic acid sodium salt (4.04 g, 40 mmol) are dissolved in dry DMSO under argon. The stirred reaction mixture is heated at 100° C. for 17 hours then poured onto water (50 ml). The white precipitate is removed by filtration and dried under vacuum to afford the title compound (2.2 g).

31b) 1-(4-Methanesulfonyl-phenyl)-propan-2-one

The title compound is prepared by the procedures described in experiments 27a and 27b, replacing 4-methylsulfanyl-benzaldehyde with 4-methanesulfonyl-benzaldehyde (31a).

31c) 6-Chloro-pyridin-3-yl)-[5-(4-methanesulfonyl-phenyl)-4-methyl-thiazol-2-yl]-amine The title compound is prepared from 1-(4-methanesulfonyl-phenyl)-propan-2-one (31b) and (6-chloro-pyridin-3-yl)-thiourea following the sequence of reactions described in Example 2.

31 d) [5-(4-Methanesulfonyl-phenyl)-4-methyl-thiazol-2-yl]-[6-(4-methyl-piperazin-1-yl)-pyridin-3-yl]-amine A stirred solution of N-methyl piperazine (0.184 g, 1.84 mmol) and (6-chloro-pyridin-3-yl)-[5-(4-methanesulfonyl-phenyl)-4-methyl-thiazol-2-yl]-amine (31c) (0.070 g, 0.184 mmol) in DMSO (2 ml) is heated in a microwave (PROLABO SYNTHEWAVE s402™) at 60% power (180 W) for 10 hours. The solvent is removed and the residue is purified by chromatography on silica eluting with ethyl acetate-methanol (9:1) to give the title compound as a yellow solid (0.096 g).

Further compounds of formula I which are also of formula XII are shown in Table 2 below, the method of preparation being described hereinafter. The table also shows mass spectrometry data. The Examples are in free form.

TABLE 2

| Ex. | $R^a$ | $R^b$ | $R^1$ | M/s MH+ |
|---|---|---|---|---|
| 32 | Cl | methanesulfonyl | 5-methyl-2-methoxypyridin-yl | 410.0 |
| 33 | Cl | sulfamoyl | 5-methylpyrazin-yl | 382.0 |
| 34 | Cl | N-(2-hydroxyethyl)sulfamoyl | 5-methylpyrazin-yl | 425.8 |
| 35 | Cl | N-(2-hydroxyethyl)sulfamoyl | 3-methyl-1H-pyrazol-yl | 413.9 |
| 36 | Cl | N-(2-hydroxyethyl)sulfamoyl | 1,3-dimethyl-pyrazol-yl | 428.1 |
| 37 | Cl | N-(2-hydroxyethyl)sulfamoyl | 1,3,5-trimethyl-pyrazol-yl | 441.9 |
| 38 | Cl | N-(2-hydroxyethyl)sulfamoyl | 2-methylthiazol-yl | 430.9 |

TABLE 2-continued

| Ex. | R$^a$ | R$^b$ | R$^1$ | M/s MH+ |
|---|---|---|---|---|
| 39 | Cl | methanesulfonamide-N-ethanol | 2-methyl-5-methylthiazole | 444.9 |
| 40 | Cl | methanesulfonyl-N,N-bis(ethanol) | 3-methylpyrazole | 457.9 |
| 41 | Cl | methanesulfonamide-N-propyl-N',N'-diethylamine | 3-methylpyrazole | 483.0 |
| 42 | H | methanesulfonamide-N-ethanol | 3-methylpyrazine | 391.4 |
| 43 | H | methanesulfonamide-N-ethanol | 3-methylpyrazole | 379.9 |
| 44 | H | sulfonamide | 3-methylpyrazine | 348.0 |
| 45 | H | sulfonamide | 3-methylpyrazole | 335.93 |
| 46 | H | sulfonamide | 2-methyl-5-ethyl-1,3,4-thiadiazole | 381.89 |
| 47 | sulfonamide | H | 2-methyl-1,3,4-thiadiazole | 353.94 |
| 48 | sulfonamide | H | 2,5-dimethylthiazole | 366.72 |
| 49 | sulfonamide | H | 3-methylpyrazole | 336.61 |
| 50 | sulfonamide | H | 2-methylthiazole | 353.61 |

TABLE 2-continued

| Ex. | Rᵃ | Rᵇ | R¹ | M/s MH+ |
|---|---|---|---|---|
| 51 | S(=O)(=O)NH₂ (methanesulfonamide) | H | 2-methyl-4-methylthiazole | 366.89 |
| 52 | S(=O)(=O)NH₂ | H | 5-methyl-1H-tetrazole | 337.90 |
| 53 | CH₃S(=O)(=O)NH-CH₂CH₂OH | H | 2-methyl-5-ethyl-1,3,4-thiadiazole | 425.96 |
| 54 | S(=O)(=O)NH₂ | H | 2-methyl-5-(2-morpholinoethyl)-1,3,4-thiadiazole | 466.98 |
| 55 | S(=O)(=O)NH₂ | H | 2-methyl-5-(2-dimethylaminoethyl)-1,3,4-thiadiazole | 424.99 |
| 56 | S(=O)(=O)NH₂ | H | 3-(5-methyl-1,3,4-thiadiazol-2-yl)propanoic acid | 425.93 |
| 57 | S(=O)(=O)NH₂ | H | ethyl 3-(5-methyl-1,3,4-thiadiazol-2-yl)propanoate | 453.94 |
| 58 | S(=O)(=O)NH₂ | H | 2-(5-methyl-1,3,4-thiadiazol-2-yl)acetic acid | 411.89 |
| 59 | S(=O)(=O)CH₃ | —CF₃ | 3-methylpyrazine | 415.19 |
| 60 | S(=O)(=O)CH₃ | —CF₃ | 3-methyl-1H-pyrazole | 402.855 |
| 61 | S(=O)(=O)CH₃ | —CF₃ | 3-(5-methyl-1,3,4-thiadiazol-2-yl)propanoic acid | 492.94 |

TABLE 2-continued

| Ex. | R$^a$ | R$^b$ | R$^1$ | M/s MH+ |
|---|---|---|---|---|
| 62 | -S(=O)$_2$CH$_3$ | —CF$_3$ | 5-methyl-1,3,4-thiadiazol-2-yl cyclohexanecarboxylic acid | 546.4 |
| 63 | -S(=O)$_2$CH$_3$ | —CF$_3$ | 5-methyl-2-(4-methylpiperazin-1-yl)-1,3,4-thiadiazole | 519.01 |
| 64 | -S(=O)$_2$CH$_3$ | —CF$_3$ | 5-methyl-2-morpholino-1,3,4-thiadiazole | 505.98 |
| 65 | -S(=O)$_2$CH$_3$ | —CF$_3$ | 2-chloro-6-methylpyrazine | 449.04 |
| 66 | -S(=O)$_2$CH$_3$ | —CF$_3$ | 2-methyl-6-(4-methylpiperazin-1-yl)pyrazine | 513.23 |
| 67 | -S(=O)$_2$CH$_3$ | —CF$_3$ | 4-(2-(5-methyl-1,3,4-thiadiazol-2-yl)ethyl)morpholine | 534.24 |
| 68 | -S(=O)$_2$CH$_3$ | F | 3-methyl-1H-pyrazole | 352.91 |
| 69 | -S(=O)$_2$CH$_3$ | F | 1,3-dimethyl-1H-pyrazole | 366.91 |
| 70 | -S(=O)$_2$CH$_3$ | F | 4-bromo-3-methyl-1H-pyrazole | 432.86 |
| 71 | -S(=O)$_2$CH$_3$ | 1-methyl-2-propyl-1H-imidazole | 3-methyl-1H-pyrazole | 442.98 |

TABLE 2-continued

| Ex. | R$^a$ | R$^b$ | R$^1$ | M/s MH+ |
|---|---|---|---|---|
| 72 | methylsulfonyl | 1-methylimidazole | 3-methyl-1H-pyrazole | 400.93 |
| 73 | methylsulfonyl | N,N-dimethyl-N',N'-diethylethylenediamine | 3-methyl-1H-pyrazole | 463.04 |
| 74 | methylsulfonyl | 1,4-dimethylpiperazine | 3-methyl-1H-pyrazole | 433.06 |
| 75 | methylsulfonyl | 1-methylimidazole | 2,5-dimethyl-1,3,4-thiadiazole | 432.99 |
| 76 | methylsulfonyl | 1-methylimidazole | 2-methylpyrazine | 413.01 |
| 77 | methylsulfonyl | 1,2-dimethylimidazole | 2-methylpyrazine | 427.02 |
| 78 | methylsulfonyl | 2-ethyl-1-methylimidazole | 2-methylpyrazine | 441.00 |
| 79 | methylsulfonyl | 2-isopropyl-1-methylimidazole | 2-methylpyrazine | 456.23 |
| 80 | methylsulfonyl | 1-methyl-2-propylimidazole | 2-ethyl-5-methyl-1,3,4-thiadiazole | 488.92 |

TABLE 2-continued

| Ex. | R$^a$ | R$^b$ | R$^1$ | M/s MH+ |
|---|---|---|---|---|
| 81 | -S(O)$_2$CH$_3$ | -OCH$_2$CH$_2$-morpholine | 3-methyl-pyrazol-5-yl (NH) | 464.27 |
| 82 | -C(O)OH | H | 3-methyl-pyrazol-5-yl (NH) | 300.97 |
| 83 | -C(O)OH | H | 3-methyl-pyrazin-2-yl | 312.97 |
| 84 | -C(O)OH | H | 2-methyl-4-methyl-thiazol-5-yl | 331.95 |

Preparation of Specific Examples

Example 32

[5-(4-Chloro-3-methanesulfonyl-phenyl)-4-methyl-thiazol-2-yl]-(6-methoxy-pyridin-3-yl)-amine 32a) 2-Chloro-5-(2-oxopropyl)-benzenesulphonyl chloride To chlorosulfonic acid (25 ml, excess) cooled at −10° C. is added dropwise 4-chlorophenyl acetone (1.0 g, 5.93 mmol). The temperature is kept below 0° C. throughout the addition. The reaction mixture is then left to warm up to room temperature overnight. The reaction mixture is poured carefully onto ice (1500 ml). Once the ice is melted, the aqueous layer is extracted with dichloromethane (3×250 ml). The combined organic layers are dried over MgSO$_4$, filtered and concentrated to afford the titled compound as an off-white solid.

32b) 1-(4-Chloro-3-methanesulfonyl-phenyl)-propan-2-one

To a stirred solution of sodium sulfite (0.5 g, 3.99 mmol) and sodium hydrogen carbonate (0.34 g, 3.99 mmol) in water (10 ml) at 70° C. is added a solution of 2-chloro-5-(2-oxopropyl)-benzenesulfonyl chloride (32a) (0.5 g, 1.87 mmol) in 1,4-dioxane (20 ml). After 1 hour the reaction mixture is concentrated to yield the sulfinate intermediate. To the sulfinate intermediate (0.47 g, 1.95 mmol) in DMF (20 ml) is added iodomethane (0.12 ml, 1.95 mmol). After 1 hour at 40° C., the reaction mixture is poured into water (400 ml) and extracted with ethyl acetate (3×100 ml). The combined organic layers are dried over MgSO$_4$, filtered and concentrated. The residue is purified by chromatography on silica, eluting with hexane/ethyl acetate (4:1), then left overnight in the vacuum oven to afford the titled compound.

32c) [5-(4-Chloro-3-methanesulfonyl-phenyl)-4-methyl-thiazol-2-yl]-(6-methoxy-pyridin-3-yl)-amine 1-(4-chloro-3-methanesulfonyl-phenyl)-propan-2-one (32b) (0.23 g, 1 mmol) is dissolved in dioxan (10 ml) and the solution is cooled to 10° C. at which point the mixture is semi-frozen. Bromine (0.045 ml, 0.8 mmol, 0.8 eq.) is added slowly and the mixture is stirred for an additional 15 minutes in a semi frozen state. The mixture is then allowed to warm to room temperature and the solvent is removed to give a brown oil containing starting material and 1-bromo-1-(3-fluoro-4-methanesulfonyl-phenyl)-propan-2-one. This material is dissolved in ethanol (10 ml). (6-Methoxy-pyridine-3-yl)-thio-urea (0.183 g, 1 mmol) is added in one portion. The mixture is stirred at 60° C. for 30 minutes then allowed to cool whereupon the product crystallised. Filtration affords the titled compound as a white solid.

Example 33

2-Chloro-5-[4-methyl-2-(pyrazin-2-ylamino)-thiazol-5-yl]-benzenesulfonamide 33a) 2-Chloro-5-(2-oxo-propyl)-benzenesulfonamide 2-Chloro-5-(2-oxopropyl)-benzenesulphonyl chloride (32a) (2.0 g, 7.5 mmol) is dissolved in dioxan (50 ml) with stirring. Sodium carbonate (7.5 ml, 2M solution, 2 eq.) is added followed by a solution of ammonia in dioxan (37.5 ml, 0.5 M). After 30 min the reaction mixture is poured onto water (250 ml) and extracted with ethyl acetate (3×100 ml). The combined organic extracts are washed with water (2×100 ml) followed by brine (100 ml) and dried (MgSO$_4$). After filtration the solvent is removed and the product is purified by chromatography on silica, eluting with ethyl acetate/hexane (1:2) to afford the titled compound.

33b) 5-(1-Bromo-2-oxo-propyl)-2-chloro-benzene-sulfonamide

A stirred solution of 2-chloro-5-(2-oxo-propyl)-benzenesulfonamide (33a) (1.4 g, 5.7 mmol) in dry THF (100 ml) at room temperature is treated with polymer supported pyridine hydrobromide perbromide (2.9 g, 5.7 mmol) and left to stir overnight. The reaction mixture is then filtered and the solvent removed in vacuo. The residue is purified by chromatography on silica eluting with 1:4 ethyl acetate-hexane to give the titled compound.

33c) 2-Chloro-5-[4-methyl-2-(pyrazin-2-ylamino)-thiazol-5-yl]-benzenesulfonamide Pyrazin-2-yl-thiourea (1a) (0.07 g, 0.57 mmol) is added to a stirred solution of 5-(1-Bromo-2-oxo-propyl)-2-chloro-benzenesulfonamide (33b) (0.15 g, 0.46 mmol) in 1,4-dioxan (10 ml) at room temperature. The reaction mixture is heated to 70° C. for 2 h. The resulting precipitate is removed by filtration and dried under vacuum to give the titled compound

Example 34

2-Chloro-N-(2-hydroxy-ethyl)-5-[4-methyl-2-(pyrazin-2-ylamino)-thiazol-5-yl]-benzenesulfonamide The titled compound is prepared by the same procedure as Example 33, replacing ammonia in this procedure with ethanolamine.

Example 35

2-Chloro-N-(2-hydroxy-ethyl)-5-[4-methyl-2-(1H-pyrazol-3-ylamino)-thiazol-5-yl]-benzenesulfonamide

35a) (1H-Pyrazol-3-yl)-thiourea

1H-Pyrazol-3-ylamine (9.5 g, 114 mmol) is added to a stirred solution of benzoyl isothiocyanate (19.6 g, 120 mmol) in DMF (100 ml) at room temperature. The solution is heated at 100° C. for 30 minutes, allowed to cool and poured onto water (1000 ml). The yellow suspension of 1-benzoyl-3-(1H-pyrazol-3-yl)-thiourea is removed by filtration and washed with water. This material is dissolved in 2M aqueous sodium hydroxide (120 ml) and the solution is heated at reflux for 30 minutes. After cooling to room temperature the solution is brought to pH 4 by addition of 3M aqueous HCl and extracted with ethyl acetate. The organic extract is dried (MgSO$_4$) and concentrated to afford the titled compound which is removed by filtration and recrystallised from dichloromethane.

35b) 2-Chloro-N-(2-hydroxy-ethyl)-5-[4-methyl-2-(1H-pyrazol-3-ylamino)-thiazol-5-yl]-benzenesulfonamide The titled compound is prepared by an analogous procedure to Example 34, replacing pyrazin-2-yl-thiourea in this procedure with (1H-pyrazol-3-yl)-thiourea (35a).

Example 36

2-Chloro-N-(2-hydroxy-ethyl)-5-[4-methyl-2-(1-methyl-1H-pyrazol-3-ylamino)-thiazol-5-yl]-benzenesulfonamide

36a) (1-Methyl-1H-pyrazol-3-yl)-thiourea

This material is prepared from 1-methyl-1H-pyrazol-3-ylamine following the procedure described for the preparation of (1H-pyrazol-3-yl)-thiourea (35a)

36b) 2-Chloro-N-(2-hydroxy-ethyl)-5-[4-methyl-2-(1-methyl-1H-pyrazol-3-ylamino)-thiazol-5-yl]-benzenesulfonamide The titled compound is prepared by an analogous procedure to Example 34, replacing pyrazin-2-yl-thiourea (1a) in this procedure with (1-methyl-1H-pyrazol-3-yl)-thiourea (36a)

Example 37

2-Chloro-5-[2-(2,5-dimethyl-2H-pyrazol-3-ylamino)-4-methyl-thiazol-5-yl]-N-(2-hydroxy-ethyl)-benzenesulfonamide

37a) (2,5-Dimethyl-2H-pyrazol-3-yl)-thiourea

This material is prepared from 2,5-dimethyl-2H-pyrazol-3-ylamine following the procedure described for (1H-pyrazol-3-yl)-thiourea (35a)

37b) 2-Chloro-5-[2-(2,5-dimethyl-2H-pyrazol-3-ylamino)-4-methyl-thiazol-5-yl]-N-(2-hydroxy-ethyl)-benzenesulfonamide The titled compound is prepared by an analogous procedure to Example 34, replacing pyrazin-2-yl-thiourea (1a) in this procedure with (2,5-dimethyl-2H-pyrazol-3-yl)-thiourea (37a).

Example 38

2-Chloro-N-(2-hydroxy-ethyl)-5-[4-methyl-2-(thiazol-2-ylamino)-thiazol-5-yl]-benzenesulfonamide

38a) Thiazol-2-yl-thiourea

Aminothiazole (1.0 g, 10 mmol is added in small portions to a stirred solution of FMOC isothiacyanate (2.92 g, 10.4 mmol) in dichloromethane (30 ml). The reaction mixture is stirred at room temperature for 18 hours. The solid material which precipitates is removed by filtration and dissolved in a solution containing 20% piperidine in methanol (10 ml). After stirring for 18 hours at room temperature the mixture is filtered and the solvent is removed from the filtrate. The residue is dissolved in ethyl acetate and washed with 2M aqueous HCl (3×40 ml). The organic layer is then separated and extracted with saturated aqueous sodium bicarbonate (3×30 ml). The aqueous extract is acidified with 2M HCl and the product is extracted into ethyl acetate. The organic extract

38b) 2-Chloro-N-(2-hydroxy-ethyl)-5-[4-methyl-2-(thiazol-2-ylamino)-thiazol-5-yl]-benzenesulfonamide The titled compound is prepared by an analogous procedure to Example 34, replacing pyrazin-2-yl-thiourea in this procedure with thiazol-2-yl-thiourea (38a).

Example 39

2-Chloro-N-(2-hydroxy-ethyl)-5-[4-methyl-2-(5-methyl-thiazol-2-ylamino)-thiazol-5-yl]-benzenesulfonamide The titled compound is prepared by the method described in Example 34, replacing pyrazin-2-yl-thiourea (1a) with (5-methyl-thiazol-2-yl)-thiourea. This thiourea is prepared by an analogous procedure to thiazol-2-thiourea (38a)

Example 40

2-Chloro-N,N-bis-(2-hydroxy-ethyl)-5-[4-methyl-2-(1H-pyrazol-3-ylamino)-thiazol-5-yl]-benzenesulfonamide The titled compound is prepared by the same procedure as Example 35, replacing ethanolamine in this procedure with 2-(2-hydroxy-ethylamino)-ethanol.

Example 41

2-Chloro-N-(3-diethylamino-propyl)-5-[4-methyl-2-(1H-pyrazol-3-ylamino)-thiazol-5-yl]-benzenesulfonamide The titled compound is prepared by the same procedure as Example 35, replacing ethanolamine in this procedure with N,N-diethyl-propane-1,3-diamine

Example 42

N-(2-Hydroxy-ethyl)-3-[4-methyl-2-(pyrazin-2-ylamino)-thiazol-5-yl]-benzene-sulfonamide

42a) 1-Bromo-1-(3-nitro-phenyl)-propan-2-one

A stirred solution of 3-nitrophenylacetone (2.5 g, 14.0 mmol) in dry THF (50 ml) at room temperature is treated with polymer supported pyridine hydrobromide perbromide (7.0 g, 14.0 mmol) and left to stir overnight. The reaction mixture is then filtered and the solvent removed in vacuo. The residue is purified by chromatography on silica eluting with 1:4 ethyl acetate-hexane to give the titled compound

42b) [4-Methyl-5-(3-nitro-phenyl)-thiazol-2-yl]-pyrazin-2-yl-amine

The titled compound is prepared by the same procedure described for the preparation of 33c, replacing 5-(1-Bromo-2-oxo-propyl)-2-chloro-benzenesulfonamide (33b) in this procedure with 1-Bromo-1-(3-nitro-phenyl)-propan-2-one (42a)

42c) 3-[4-Methyl-2-(pyrazin-2-ylamino)-thiazol-5-yl]-benzenesulfonyl chloride

[4-Methyl-5-(3-nitro-phenyl)-thiazol-2-yl]-pyrazin-2-yl-amine (42b) (1.079 g, 3.4 mmol) is dissolved in ethyl acetate/THF (5/1, 240 ml) and stirred at room temperature under an atmosphere of argon. The solution is then treated with 10% Pd/C (1.1 g). The reaction mixture is purged three times with nitrogen and placed under an atmosphere of hydrogen overnight. The mixture is then filtered through celite and the catalyst is washed with THF (200 ml). The solvent is removed in vacuo to leave [5-(3-amino-phenyl)-4-methyl-thiazol-2-yl]-pyrazin-2-yl-amine (0.351 g, 36%). MH$^+$ (ESMS):283.5

Concentrated sulfuric acid (1 ml) is added slowly to a stirred solution of [5-(3-amino-phenyl)-4-methyl-thiazol-2-yl]-pyrazin-2-yl-amine (0.351 g, 1.24 mmol) in acetic acid (20 ml) at 10° C. A solution of sodium nitrite (0.09 g, 1.24 mmol) in water (0.5 ml) is added dropwise. After 10 minutes a solution of the reagent ($SO_2$/AcOH/$CuCl_2$/$H_2O$) (50 ml) at 0° C. is added and the mixture is allowed to warm to room temperature and stirred for overnight. The mixture is diluted with water (100 ml) and extracted with ethylacetate (3×100 ml). The organic extracts are combined, washed with brine (100 ml), dried ($MgSO_4$), filtered and the solvent is removed to afford the title compound (0.251 g, 55%) which is used crude in the subsequent reaction.

42d) N-(2-Hydroxy-ethyl)-3-[4-methyl-2-(pyrazin-2-ylamino)-thiazol-5-yl]-benzenesulfonamide 3-[4-Methyl-2-(pyrazin-2-ylamino)-thiazol-5-yl]-benzenesulfonyl chloride (42c) (0.251 g, 0.68 mmol) is dissolved in dioxane (10 ml). The solution is treated with 2M aqueous sodium carbonate (0.7 ml, 1.36 mmol) followed by the addition of ethanolamine (0.125 ml, 2.05 mmol). The reaction mixture is stirred overnight. The solvent is removed in vacuo and the residue is taken into water (10 ml)/ethylacetate (30 ml) and sonicated. The layers are separated then the aqueous layer is extracted with ethyl acetate (2×30 ml). The combined organic layers are dried over $MgSO_4$, filtered and concentrated to give a residue which is purified by prep LC-MS to give the titled compound (0.038 g, 14%)

Example 43

N-(2-Hydroxy-ethyl)-3-[4-methyl-2-(1H-pyrazol-3-ylamino)-thiazol-5-yl]-benzenesulfonamide

43a) 2-Chloro-N-(2-hydroxy-ethyl)-5-(2-oxo-propyl)-benzenesulfonamide

This material is prepared from 2-chloro-5-(2-oxopropyl)-benzenesulphonyl chloride (32a) following the same procedure described for the preparation of 2-chloro-5-(2-oxo-propyl)-benzenesulfonamide (33a), replacing ammonia in this procedure with ethanolamine.

43b) N-(2-Hydroxy-ethyl)-3-(2-oxo-propyl)-benzenesulfonamide

2-Chloro-N-(2-hydroxy-ethyl)-5-(2-oxo-propyl)-benzenesulfonamide (43b) (1.22 g, 4.18 mmol) in methanol (150 ml) is stirred under an atmosphere of hydrogen in the presence of 10% Palladium on carbon (1 g) for 5 hours at room temperature. Filtration through celite and removal of the solvent affords the titled compound which is purified by chromatography on silica eluting with ethyl acetate-hexane (2:1).

43c) N-(2-Hydroxy-ethyl)-3-[4-methyl-2-(1H-pyrazol-3-ylamino)-thiazol-5-yl]-benzenesulfonamide The titled compound was prepared from N-(2-hydroxyethyl)-3-(2-oxo-propyl)-benzenesulfonamide (43b) following the two-step procedure (bromination, thiazole formation) described for the conversion of 2-chloro-5-(2-oxo-propyl)-benzene-sulfonamide (33a) to 2-chloro-5-[4-methyl-2-(pyrazin-2-ylamino)-thiazol-5-yl]-benzenesulfonamide (33c) replacing pyrazin-2-yl-thiourea (1a) in the final step with (1H-pyrazol-3-yl)-thiourea (35a).

Example 44

3-[4-Methyl-2-(pyrazin-2-ylamino)-thiazol-5-yl]-benzenesulfonamide

The titled compound is prepared by an analogous procedure to N-(2-hydroxy-ethyl)-3-[4-methyl-2-(pyrazin-2-ylamino)-thiazol-5-yl]-benzenesulfonamide (Example 42 using ammonia in place of ethanolamine in the final step.

Example 45 and 46

The compounds of these Examples, namely 3-[4-methyl-2-(1H-pyrazol-3-ylamino)-thiazol-5-yl]-benzenesulfonamide and 3-[2-(5-ethyl-[1,3,4]thiadiazol-2-ylamino)-4-methyl-thiazol-5-yl]-benzenesulfonamide respectively are prepared by the route described for N-(2-hydroxy-ethyl)-3-[4-methyl-2-(1H-pyrazol-3-ylamino)-thiazol-5-yl]-benzenesulfonamide (Example 43) using the appropriate amine and thiourea. The thiourea used in Example 46 is prepared by an analogous procedure to thiazol-2-yl-thiourea Example (38a).

Examples 47 to 58

The compounds of these Examples, namely 4-[4-methyl-2-([1,3,4]thiadiazol-2-ylamino)-thiazol-5-yl]-benzene-sulfonamide, 4-[4-methyl-2-(5-methyl-thiazol-2-ylamino)-thiazol-5-yl]-benzenesulfonamide, 4-[4-methyl-2-(1H-pyrazol-3-ylamino)-thiazol-5-yl]-benzenesulfonamide, 4-[4-methyl-2-(thiazol-2-ylamino)-thiazol-5-yl]-benzene-sulfonamide, 4-[4-methyl-2-(4-methyl-thiazol-2-ylamino)-thiazol-5-yl]-benzenesulfonamide, 4-[4-methyl-2-(1H-tetrazol-5-ylamino)-thiazol-5-yl]-benzenesulfonamide and 4-[2-(5-ethyl-[1,3,4]thiadiazol-2-ylamino)-4-methyl-thiazol-5-yl]-N-(2-hydroxy-ethyl)-benzenesulfonamide respectively are prepared in a three step sequence from 4-(2-oxo-propyl)-benzenesulfonyl chloride (prepared as described in European patent specification EP 91749 A2) following the procedures described in Example 1, using the appropriate amines and thioureas. Thioureas used in Examples 47, 48, 50, 51 & 53 are prepared from the appropriate amino heterocycle using the FMOC procedure described for thiazol-2-yl-thiourea (Example 38a) Thioureas used in Examples 49 and 52 are prepared as described for (1H-pyrazol-3-yl)-thiourea (35a). The preparation of thioureas used in Examples 54, 55, 56, 57 & 58 are described for each of these Examples.

Example 54

4-{4-Methyl-2-[5-(2-morpholin-4-yl-ethyl)-[1,3,4]thiadiazol-2-ylamino]-thiazol-5-yl}-benzenesulfonamide 54a) 5-(2-Chloro-ethyl)-[1,3,4]thiadiazol-2-ylamine Thiosemicarbazide (10 g, 111 mmol) is added in portions to a solution of 3-chloropropionic acid (10 g, 92 mmol) in concentrated sulfuric acid. The mixture is heated with stirring at 75° C. for 1 hour. After cooling to room temperature the reaction mixture id added slowly to water and the resulting solution is brought to pH 7 by addition of aqueous ammonia solution. The titled product precipitates as a yellow solid which is removed by filtration and dried.

54b) 5-(2-Morpholin-4-yl-ethyl)-[1,3,4]thiadiazol-2-ylamine

A mixture of 5-(2-chloro-ethyl)-[1,3,4]thiadiazol-2-ylamine (54a) (2.5 g, 15.3 mmol), morpholine (2.67 g, 30 mmol) and sodium iodide (0.15 g) is heated with stirring in toluene at 80° C. After adding triethylamine (2.13 ml, 15.3 mmol) heating is continued for an additional 4 hours. The solvent is removed and the residue is partitioned between water (pH 13) and n-butanol. The organic extract is dried ($MgSO_4$) and the solid is removed to afford the titled compound as a yellow solid.

54c) [5-(2-Morpholin-4-yl-ethyl)-[1,3,4]thiadiazol-2-yl}-thiourea

The titled compound is prepared from 5-(2-Morpholin-4-yl-ethyl)-[1,3,4]thiadiazol-2-ylamine (54b) following the procedure described for (1H-pyrazol-3-yl)-thiourea (35a)

54d) 4-{4-Methyl-2-[5-(2-morpholin-4-yl-ethyl)-[1,3,4]thiadiazol-2-ylamino]-thiazol-5-yl}-benzene-sulfonamide The titled compound is prepared from 4-(2-oxo-propyl)-benzenesulfonyl chloride (prepared as described in European patent specification EP 91749 A2) following the procedures described in Example 1, using ammonia and [5-(2-morpholin-4-yl-ethyl)-[1,3,4]thiadiazol-2-yl}-thiourea (54c).

Example 55

4-{2-[5-(2-Dimethylamino-ethyl)-[1,3,4]thiadiazol-2-ylamino]-4-methyl-thiazol-5-yl}-benzenesulfonamide The titled compound is prepared following the procedures described in Example 54, replacing morpholine in the above procedures with dimethylamine.

Example 56

3-{5-[4-Methyl-5-(4-sulfamoyl-phenyl)-thiazol-2-ylamino]-[1,3,4]thiadiazol-2-yl}-propionic acid 56a) 3-(5-Amino-[1,3,4]thiadiazol-2-yl)-propionic acid methyl ester 3-Chlorocarbonyl-propionic acid methyl ester (4.4 g, 21 mmol) is added dropwise to a stirred suspension of thiosemicarbazide (4.0 g, 44 mmol) in THF (25 ml) at 0° C. After stirring at room temperature for 18 h the product which precipitates is removed by filtration and washed with diethyl ether. This product (7.1 g, 34 mmol) is suspended in toluene (30 ml) at 0° C. and methane sulfonic acid (3.37 ml, 52 mmol) is added dropwise to the stirred reaction. The reaction is heated at 70° C. for 3 hours then concentrated at reduced pressure. Methanol (30 ml) is added followed by slow addition of aqueous ammonia, with stirring, until the solution is basic. The titled compound which precipitates is removed by filtration and purified by chromatography on silica, eluting with chloroform-methanol (10:1).

56b)
3-(5-Thioureido-[1,3,4]thiadiazol-2-yl)-propionic acid

Ethoxycarbonyl isothiocyanate (0.656 ml, 5.61 mmol) is added dropwise to a stirred suspension of 3-(5-amino-[1,3,4] thiadiazol-2-yl)-propionic acid methyl ester (56a) in dichloromethane (30 ml). The reaction is at room temperature for 18 hours. After removing the solvent, aqueous sodium hydroxide (2M, 10 ml) is added and the stirred mixture is heated at reflux for 3 hours. The solution is allowed to cool to room temperature and brought to pH 3 by the addition of 6M aqueous HCl. The titled compound which precipitates is removed by filtration, washed with ethyl acetate and dried in vacuo.

56c) 3-{5-[4-Methyl-5-(4-sulfamoyl-phenyl)-thiazol-2-ylamino]-[1,3,4]thiadiazol-2-yl}-propionic acid The titled compound is prepared from 3-(5-thioureido-[1,3,4]thiadiazol-2-yl)-propionic acid (56b) and from 4-(2-oxo-propyl)-benzenesulfonyl chloride (prepared as described in European patent specification EP 91749 A2) following procedures described for Example 1 using ammonia to prepare the sulfonamide.

Example 57

3-{5-[4-Methyl-5-(4-sulfamoyl-phenyl)-thiazol-2-ylamino]-[1,3,4]thiadiazol-2-yl}-propionic acid ethyl ester The titled compound is obtained as a minor component during the final step in the preparation of 3-{5-[4-Methyl-5-(4-sulfamoyl-phenyl)-thiazol-2-ylamino]-[1,3,4]thiadiazol-2-yl}-propionic acid (56c). This involves formation of (56c) in ethanol at reflux in the presence of anhydrous HBr which is generated during the reaction.

Example 58

{5-[4-Methyl-5-(4-sulfamoyl-phenyl)-thiazol-2-ylamino]-[1,3,4]thiadiazol-2-yl}-acetic acid The titled compound is prepared by an analogous procedure to 3-{5-[4-methyl-5-(4-sulfamoyl-phenyl)-thiazol-2-ylamino]-[1,3,4]thiadiazol-2-yl}-propionic acid Example (46) using methyl malonyl chloride in place of 3-chlorocarbonyl-propionic acid methyl ester in the first step.

Example 59

[5-(4-Methanesulfonyl-3-trifluoromethyl-phenyl)-4-methyl-thiazol-2-yl]-pyrazin-2-yl-amine

59a)
4-Methanesulfonyl-3-trifluoromethyl-benzaldehyde

Methane sulfinic acid sodium salt (6.65 g, 65.1 mmol) is added to a stirred solution of 4-Fluoro-3-trifluoromethyl-benzaldehyde (10.0 g, 52.1 mmol) in dry DMSO (200 ml) and the mixture is heated at 75° C. After 2 hours the reaction is allowed to cool and poured onto ice-water (300 ml). The precipitate is collected by filtration, washed with water and dissolved in dichloromethane (200 ml). The organic extract is washed with water (3×200 ml), dried over $MgSO_4$, filtered, and the solvent is removed to give the title compound as a white solid.

59b) 1-Methanesulfonyl-4-(2-nitro-propenyl)-2-trifluoromethyl-benzene

A stirred mixture of 4-methanesulfonyl-3-trifluoromethyl-benzaldehyde (Example 5001a) (12 g, 47 mmol), nitroethane (27.5 ml, 380 mol) and ammonium acetate (1.22 g, 16 mmol) is heated at reflux under argon for 18 hours. The mixture is concentrated to give an oil which is dissolved in dichloromethane (200 ml) and washed with water (3×200 ml), followed by brine (200 ml). The organic extract is dried ($MgSO_4$), filtered and the solvent removed to give the product as red oil. This is used immediately in the next step.

59c) 1-(4-Methanesulfonyl-3-trifluoromethyl-phenyl)-propan-2-one

A solution of freshly prepared 1-methanesulfonyl-4-(2-nitro-propenyl)-2-trifluoromethyl-benzene (59b) (14 g, 45 mmol) in acetic acid (100 ml) is added slowly to a stirred slurry of Iron powder (27.6 g, 495 mmol) in acetic acid (100 ml) at 60° C. The reaction is then stirred at 100° C. for 2 hours then allowed to cool and poured onto ice-water (300 ml). After filtration through celite, washing with dichloromethane (500 ml), the organic extract is separated and washed with water (3×300 ml) followed by brine (500 ml). The organic extract is dried ($MgSO_4$) and concentrated to give a red oil. Chromatography on silica, eluting with ethyl acetate-hexane, affords the titled compound as a white solid.

59d) [5-(4-Methanesulfonyl-3-trifluoromethyl-phenyl)-4-methyl-thiazol-2-yl]-pyrazin-2-yl-amine 1-(4-Methanesulfonyl-3-trifluoromethyl-phenyl)-propan-2-one (Example 59c) (0.60 g, 2.14 mmol) is dissolved in dioxan (50 ml) and the solution is cooled to 10° C. at which point the mixture is semi frozen. Bromine (0.088 ml, 1.7 mmol) is added slowly and the mixture is stirred for an additional 30 min in a semi frozen state. The mixture is then allowed to warm to room temperature and the solvent is removed to give a brown oil. This material is dissolved in ethanol and pyrazin-2-yl-thiourea (1a) is added in one portion. The mixture is stirred at 60° C. for 30 minutes then allowed to cool whereupon the titled product precipitates and is removed by filtration.

Example 60

[5-(4-Methanesulfonyl-3-trifluoromethyl-phenyl)-4-methyl-thiazol-2-yl]-(1H-pyrazol-3-yl)-amine The titled compound is prepared by an analogous procedure to Example 50, replacing pyrazin-2-yl-thiourea (1a) with (1H-pyrazol-3-yl)-thiourea (3402a).

Example 61

3-{5-[5-(4-Methanesulfonyl-3-trifluoromethyl-phenyl)-4-methyl-thiazol-2-ylamino]-[1,3,4]thiadiazol-2-yl}-propionic acid The titled compound is prepared by an analogous procedure to Example 59, replacing pyrazin-2-yl-thiourea (1a) with 3-(5-thioureido-[1,3,4]thiadiazol-2-yl)-propionic acid (56b)

Example 62

4-{5-[5-(4-Methanesulfonyl-3-trifluoromethyl-phenyl)-4-methyl-thiazol-2-ylamino]-[1,3,4]thiadiazol-2-yl}-cyclohexanecarboxylic acid The titled compound is prepared by an analogous procedure to Example 59, replacing pyrazin-2-yl-thiourea (1a) with 4-(5-thioureido-[1,3,4]thiadiazol-2-yl)-cyclohexanecarboxylic acid. This thiourea is prepared in an identical procedure to 3-(5-thioureido-[1,3,4]thiadiazol-2-yl)-propionic acid (56b), substituting 3-chlorocarbonyl-propionic acid methyl ester for 4-chlorocarbonyl-cyclohexanecarboxylic acid methyl ester in the first step.

Example 63

[5-(4-Methanesulfonyl-3-trifluoromethyl-phenyl)-4-methyl-thiazol-2-yl]-[5-(4-methyl-piperazin-1-yl)-[1,3,4]thiadiazol-2-yl]-amine

63a) 5-Bromo-[1,3,4]thiadiazol-2-ylamine

Bromine (2.1 ml, 41.5 mmol) is added to a stirred solution of 2-amino-1,3,4-thiadiazole (2.8 g, 27.7 mmol) in methanol (100 ml). After 18 hours the solvent is removed and the residue is partitioned between ethyl acetate (100 ml) and aqueous NaOH (1M, 100 ml). The organic extract is separated, washed with brine (100 ml) and dried over $MgSO_4$. The solvent is removed to afford the titled compound.

63b) 5-(4-Methyl-piperazin-1-yl)-[1,3,4]thiadiazol-2-ylamine

A mixture of 1-methylpiperazine (0.742 ml, 6.6 mmol) and bromo-[1,3,4]thiadiazol-2-ylamine (63a) (0.60 g, 3.3 mmol) in n-propanol (15 ml) is heated at reflux for 6 hours. After cooling to room temperature the solvent is removed and the residue is triturated with ethyl acetate and methanol to afford the required compound as a pink solid.

63c) [5-(4-Methyl-piperazin-1-yl)-[1,3,4]thiadiazol-2-yl]-thiourea

Ethoxycarbonylisothiocyanate (0.346 ml, 2.96 mmol) is added dropwise to a stirred suspension of 5-(4-Methyl-piperazin-1-yl)-[1,3,4]thiadiazol-2-ylamine (63b) (0.59 g, 2.96 mmol) in acetonitrile (15 ml) and DMF (5 ml). The reaction is heated at 80° C. for 7 h followed by removal of the solvent. The residue heated in 2M aqueous NaOH (80 ml) at reflux for 30 minutes. After cooling to room temperature the solution is neutralised by addition of 6M aqueous HCl and the titled product is removed by filtration and dried under vacuum.

63d) [5-(4-Methanesulfonyl-3-trifluoromethyl-phenyl)-4-methyl-thiazol-2-yl]-[5-(4-methyl-piperazin-1-yl)-[1,3,4]thiadiazol-2-yl]-amine The titled compound is prepared by an analogous procedure to Example 59, replacing pyrazin-2-yl-thiourea (1a) with [5-(4-methyl-piperazin-1-yl)-[1,3,4]thiadiazol-2-yl]-thiourea (63c).

Example 64

[5-(4-Methanesulfonyl-3-trifluoromethyl-phenyl)-4-methyl-thiazol-2-yl]-(5-morpholin-4-yl-[1,3,4]thiadiazol-2-yl)-amine The titled compound is prepared by an analogous procedure to Example 63, substituting 1-methyl-piperazine for morpholine.

Example 65

(6-Chloro-pyrazin-2-yl)-[5-(4-methanesulfonyl-3-trifluoromethyl-phenyl)-4-methyl-thiazol-2-yl]-amine The titled compound is prepared from 1-(4-methanesulfonyl-3-trifluoromethyl-phenyl) propan-2-one (59c) and 6-chloro-pyrazin-2-yl-thiourea.

Example 66

[5-(4-Methanesulfonyl-3-trifluoromethyl-phenyl)-4-methyl-thiazol-2-yl]-(4-methyl-3,4,5,6-tetrahydro-2H-[1,2']bipyrazinyl-6'-yl)-amine The titled compound is prepared from (6-chloro-pyrazin-2-yl)-[5-(4-methanesulfonyl-3-trifluoromethyl-phenyl)-4-methyl-thiazol-2-yl]-amine (65) and 1-methyl piperazine following the procedure described in Example 13.

Example 67

[5-(4-Methanesulfonyl-3-trifluoromethyl-phenyl)-4-methyl-thiazol-2-yl]-[5-(2-morpholin-4-yl-ethyl)-[1,3,4]thiadiazol-2-yl]-amine The titled compound is prepared by an analogous procedure to Example 54, replacing 4-(2-oxo-propyl)-benzenesulfonamide with 1-(4-methanesulfonyl-3-trifluoromethyl-phenyl)-propan-2-one (59c).

Example 68

[5-(3-Fluoro-4-methanesulfonyl-phenyl)-4-methyl-thiazol-2-yl]-(1H-pyrazol-3-yl-amine

68a) 3-Fluoro-4-methanesulfonyl-benzaldehyde

Methane sulfinic acid sodium salt (22.65 g, 220 mmol) is added to a stirred solution of 3,4-difluorobenzaldehyde (25 g, 175 mmol) in dry DMSO (200 ml). The mixture is heated at 65-70° C. for 5 hours then poured onto ice-water (500 ml). The precipitate is filtered, washed with water and dissolved in chloroform (400 ml). The organic extract is washed with water (2×200 ml), dried over $MgSO_4$, filtered and concentrated to give the titled compound as a white solid.

68b) 2-Fluoro-1-methanesulfonyl-4-(2-nitro-propenyl)-benzene

A stirred mixture of 3-fluoro-4-methanesulfonyl-benzaldehyde (Example 68a) (20 g, 99 mmol), nitroethane (58 ml, 811 mmol) and ammonium acetate (2.29 g, 29 mmol) is heated at reflux (115° C.) under argon for 18 hours. The mixture is concentrated to give an oil which is dissolved in chloroform (200 ml) and washed with water (2×200 ml), followed by brine (100 ml). The organic extract is dried (MgSO$_4$), filtered and the solvent removed to give the product as an orange oil. This is used immediately in the next step.

68c) 1-(3-Fluoro-4-methanesulfonyl-phenyl)-propan-2-one

Freshly prepared 2-fluoro-1-methanesulfonyl-4-(2-nitropropenyl)-benzene (Example 68b) (20 g, 77 mmol) in glacial acetic acid (150 ml) is added slowly in 15×10 ml portions to a stirred slurry of iron powder (46 g, 833 mmol) in glacial acetic acid (150 ml) at 60° C. The reaction mixture is heated at 100° C. for an additional 2 hours, allowed to cool to room temperature and poured on to ice water (600 ml). The mixture is filtered through celite to remove iron residues, washing with dichloromethane (300 ml). The organic layer is removed and the aqueous solution is extracted with more DCM (3×200 ml). The combined organic extracts are dried (MgSO$_4$), filtered and concentrated to a red solution. The titled product crystallises from this solution on standing.

68d) [5-(3-Fluoro-4-methanesulfonyl-phenyl)-4-methyl-thiazol-2-yl]-(1H-pyrazol-3-yl)-amine 1-(3-Fluoro-4-methanesulfonyl-phenyl)-propan-2-one (68c) (6.0 g, 26 mmol) is dissolved in dioxan (50 ml) and the solution is cooled to 10° C. at which point the mixture is semi frozen. A solution of bromine (0.9 ml, 17 mmol) in chloroform (2 ml) is added slowly over 30 minutes and the mixture is stirred for an additional 15 minutes in a semi frozen state. The mixture is then allowed to warm to room temperature and the solvent is removed to give a red oil. Ethanol (70 ml) and (1H-pyrazol-3-yl)-thiourea (35a) (3.2 g, 22 mmol) are added and the reaction is stirred at 60° C. for 30 minutes. The solution is allowed to cool to room temperature whereupon the product crystallises. Filtration affords the titled compound.

Example 69

[5-(3-Fluoro-4-methanesulfonyl-phenyl)-4-methyl-thiazol-2-yl]-(1H-methyl-1H-pyrazol-3-yl)-amine The titled material is prepared by an analogous procedure to Example 68, replacing (1H-pyrazol-3-yl)-thiourea (35a) in this procedure with (1-methyl-1H-pyrazol-3-yl)-thiourea (36a).

Example 70

(4-Bromo-1H-pyrazol-3-yl)-[5-(3-fluoro-4-methanesulfonyl-phenyl)-4-methyl-thiazol-2-yl]-amine Bromine (0.012 ml, 0.23 mmol) in chloroform (0.5 ml) is added dropwise to a stirred solution of [5-(3-Fluoro-4-methanesulfonyl-phenyl)-4-methyl-thiazol-2-yl]-(1H-pyrazol-3-yl)-amine (69) (0.10 g, 0.23 mmol) in chloroform (1 ml) and methanol (2 ml). After stirring at room temperature for 1 hour the hydrobromide salt of the titled compound precipitates. This is removed by filtration and washed with ether.

Example 71

{5-[4-Methanesulfonyl-3-(2-propyl-imidazol-1-yl)-phenyl]4-methyl-thiazol-2-yl}-(1H-pyrazol-3-yl)-amine A stirred mixture of [5-(3-fluoro-4-methanesulfonyl-phenyl)-4-methyl-thiazol-2-yl]-(1H-pyrazol-3-yl)-amine hydrobromide salt (68d) (1.0 g, 2.3 mmol), Caesium carbonate (1.50 g, 4.6 mmol) and 2-propylamidazole (0.508 g, 4.6 mmol) in dry DMSO (10 ml) is heated at 140° C. for 6 hours. After cooling to room temperature the mixture is diluted with ethyl acetate (50 ml) and washed with water (100 ml). The organic extract is separated and the crude product is absorbed on silica. Purification by chromatography on silica, eluting with ethyl acetate-ethanol (1:1) affords the titled compound.

Examples 72-81

The compounds of these Examples, namely [5-(3-imidazol-1-yl-4-methanesulfonyl-phenyl)-4-methyl-thiazol-2-yl]-(1H-pyrazol-3-yl)-amine, N,N-diethyl-N'-(2-methanesulfonyl-5-[4-methyl-2-(1H-pyrazol-3-ylamino)-thiazol-5-yl]-phenyl)-N'-methyl-ethane-1,2-diamine, {5-[4-methanesulfonyl-3-(4-methyl-piperazin-1-yl)-phenyl]-4-methyl-thiazol-2-yl}-(1H-pyrazol-3-yl)-amine, [5-(3-imidazol-1-yl-4-methanesulfonyl-phenyl)-4-methyl-thiazol-2-yl]-(5-methyl-[1,3,4]thiadiazol-2-yl)-amine, [5-(3-Imidazol-1-yl-4-methanesulfonyl-phenyl)-4-methyl-thiazol-2-yl]-pyrazin-2-yl-amine, (5-[4-methanesulfonyl-3-(2-methyl-imidazol-1-yl)-phenyl]4-methyl-thiazol-2-yl)-pyrazin-2-yl-amine, {5-[3-(2-ethyl-imidazol-1-yl)-4-methanesulfonyl-phenyl]-4-methyl-thiazol-2-yl}-pyrazin-2-yl-amine, {5-[3-(2-isopropyl-imidazol-1-yl)-4-methanesulfonyl-phenyl]-4-methyl-thiazol-2-yl}-pyrazin-2-yl-amine, (5-ethyl-[1,3,4]thiadiazol-2-yl)-(5-[4-methanesulfonyl-3-(2-propyl-imidazol-1-yl)-phenyl]-4-methyl-thiazol-2-yl)-amine and {5-[4-methanesulfonyl-3-(2-morpholin-4-yl-ethoxy)-phenyl]-4-methyl-thiazol-2-yl}-(1H-pyrazol-3-yl)-amine respectively, are prepared from the appropriate amine or alcohol and fluorinated phenyl-aminothiazole following the procedure described in Example 71 and using a reaction temperature of 100 to 150° C. The fluorinated phenyl-amino-thiazoles used in these Examples are prepared from 1-(3-fluoro-4-methane-sulfonyl-phenyl)-propan-2-one (Example 68c) and the appropriate thiourea following the procedure described in Example 68d.

Examples 82 to 84

The compounds of these Examples, namely 4-[4-methyl-2-(1H-pyrazol-3-ylamino)-thiazol-5-yl]-benzoic acid, 4-[4-methyl-2-(pyrazin-2-ylamino)-thiazol-5-yl]-benzoic acid and 4-[4-methyl-2-(5-methyl-thiazol-2-ylamino)-thiazol-5-yl]-benzoic acid are prepared from 4-(2-oxo-propyl)benzoic acid and the appropriate aminothiazole following the bromination-thiazole formation procedures described in Example 65.

The invention claimed is:
1. A compound of formula I

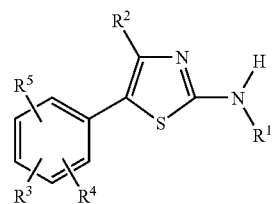

in free or salt form, wherein
R$^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_8$-alkyl optionally substituted by —$NR^6R^7$, carboxy, $C_1$-$C_8$-alkoxycarbonyl or a 5 or 6-membered heterocyclic ring containing at least one hetero atom selected from the group consisting of nitrogen, oxygen and sulphur, that ring being optionally substituted by $C_1$-$C_8$-alkoxy, —$NR^6R^7$, $C_3$-$C_8$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_8$-alkyl;

$R^2$ is $C_1$-$C_8$-alkyl or halo;

$R^3$ is —$SO_2NR^8R^9$, —$SOR^{10}$ or —$SO_2R^{11}$ and is in the para or meta position with respect to the indicated thiazole ring;

$R^4$ and $R^5$ are each independently hydrogen, $C_1$-$C_8$-alkyl, $C_1$-$C_8$-alkoxy optionally substituted by a 5 or 6-membered heterocyclic ring containing at least one hetero atom selected from the group consisting of nitrogen, oxygen and sulphur, that ring being optionally substituted by halo, halo-$C_1$-$C_8$-alkyl, cyano, —$SO_2NH_2$, carboxy, amino, amino-$C_1$-$C_8$-alkyl, di($C_1$-$C_8$-alkyl)amino-$C_1$-$C_8$-alkyl, amino-$C_1$-$C_8$-alkoxy, di($C_1$-$C_8$-alkyl)amino-$C_1$-$C_8$-alkoxy, aminocarbonyl, $C_1$-$C_8$-alkylaminocarbonyl, di($C_1$-$C_8$-alkyl)aminocarbonyl, —$NR^{12}R^{13}$, carboxy-$C_1$-$C_8$-alkyl, carboxy-$C_1$-$C_8$-alkoxy, $R^{14}$, —$OR^{14}$ or a 5 or 6-membered heterocyclic ring containing at least one hetero atom selected from the group consisting of nitrogen, oxygen and sulphur, that ring being optionally substituted by $C_1$-$C_8$-alkyl;

$R^6$ is hydrogen or $C_1$-$C_8$-alkyl;

$R^7$ is $C_1$-$C_8$-alkyl optionally substituted by hydroxy, $C_1$-$C_8$-alkoxy, di($C_1$-$C_8$-alkyl)amino or a 5 or 6-membered heterocyclic ring containing at least one hetero atom selected from the group consisting of nitrogen, oxygen and sulphur, that ring being optionally substituted by $C_1$-$C_8$-alkyl;

$R^8$ is hydrogen or $C_1$-$C_8$-alkyl optionally substituted by hydroxy, $C_1$-$C_8$-alkoxy, cyano, amino, $C_1$-$C_8$-alkylamino, di($C_1$-$C_8$-alkyl)amino or a 5 or 6-membered heterocyclic ring having one or more ring hetero atoms selected from the group consisting of oxygen, nitrogen and sulphur, that ring being optionally substituted by $C_1$-$C_8$-alkyl;

$R^9$ is hydrogen, $C_1$-$C_8$-alkyl optionally substituted by hydroxy, or $C_3$-$C_8$-cycloalkyl;

$R^{10}$ is $C_1$-$C_8$-alkyl;

$R^{11}$ is $C_1$-$C_8$-alkyl optionally substituted by halogen, hydroxy, $C_1$-$C_8$-alkoxy, cyano, amino, $C_1$-$C_8$-alkylamino or di($C_1$-$C_8$-alkyl)amino;

$R^{12}$ is hydrogen or $C_1$-$C_8$-alkyl;

$R^{13}$ is $C_1$-$C_8$-alkyl or $C_3$-$C_8$-cycloalkyl optionally substituted by hydroxy, amino, $C_1$-$C_8$-alkylamino or di($C_1$-$C_8$-alkyl)amino or $R^{12}$ and $R^{13}$ together with the nitrogen atom to which they are attached form a 5 or 6-membered saturated or unsaturated heterocyclic ring that contains one or more further hetero atoms selected from the group consisting of oxygen, nitrogen and sulphur, that ring being optionally substituted by $C_1$-$C_8$-alkyl; and $R^{14}$ is $C_1$-$C_8$-alkyl optionally substituted by hydroxy or —$NR^{12}R^{13}$.

2. A compound according to claim 1, in free or salt form, wherein $R^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_8$-alkyl optionally substituted by —$NR^6R^7$, carboxy, $C_1$-$C_8$-alkoxycarbonyl or a 5 or 6-membered heterocyclic ring containing at least one hetero atom selected from the group consisting of nitrogen, oxygen and sulphur, $C_1$-$C_8$-alkoxy, —$NR^6R^7$, $C_3$-$C_8$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_8$-alkyl;

$R^2$ is $C_1$-$C_8$-alkyl;

$R^3$ is —$SO_2NR^8R^9$, —$SOR^{10}$, or —$SO_2R^{11}$ and is in the para or meta position with respect to the indicated thiazole ring;

$R^4$ is hydrogen, $C_1$-$C_8$-alkoxy optionally substituted by a 5 or 6-membered heterocyclic ring containing at least one hetero atom selected from the group consisting of nitrogen, oxygen and sulphur, that ring being optionally substituted by halo, halo-$C_1$-$C_8$-alkyl, —$SO_2NH_2$, —$NR^{12}R^{13}$ or a 5 or 6-membered heterocyclic ring containing at least one hetero atom selected from the group consisting of nitrogen, oxygen and sulphur, that ring being optionally substituted by $C_1$-$C_8$-alkyl;

$R^5$ is hydrogen;

$R^6$ is hydrogen or $C_1$-$C_8$-alkyl;

$R^7$ is $C_1$-$C_8$-alkyl optionally substituted by hydroxy, di($C_1$-$C_8$-alkyl)amino or a 5 or 6-membered heterocyclic ring containing at least one hetero atom selected from the group consisting of nitrogen and oxygen, that ring being optionally substituted by $C_1$-$C_8$-alkyl;

$R^8$ is hydrogen or $C_1$-$C_8$-alkyl optionally substituted by di($C_1$-$C_8$-alkyl)amino;

$R^9$ is hydrogen, $C_1$-$C_8$-alkyl optionally substituted by hydroxy, or $C_3$-$C_8$-cycloalkyl;

$R^{10}$ is $C_1$-$C_8$-alkyl;

$R^{11}$ is $C_1$-$C_8$-alkyl;

$R^{12}$ is $C_1$-$C_8$-alkyl; and $R^{13}$ is $C_1$-$C_8$-alkyl optionally substituted by di($C_1$-$C_8$-alkyl)amino.

3. A compound according to claim 2, in free or salt form, wherein $R^1$ is a 5 or 6-membered heterocyclic ring containing nitrogen and optionally one or more further hetero atoms selected from the group consisting of nitrogen, oxygen and sulphur, that ring being optionally substituted by halo, $C_1$-$C_4$-alkyl optionally substituted by —$NR^6R^7$, carboxy, $C_1$-$C_4$-alkoxycarbonyl or a 5 or 6-membered heterocyclic ring containing at least one hetero atom selected from the group consisting of nitrogen, oxygen and sulphur, $C_1$-$C_4$-alkoxy, —$NR^6R^7$, $C_3$-$C_6$-cycloalkyl optionally substituted by carboxy, or a 5 or 6-membered heterocyclic ring containing at least one hetero atom selected from the group consisting of nitrogen and oxygen, that ring being optionally substituted by $C_1$-$C_4$-alkyl;

$R^2$ is $C_1$-$C_4$-alkyl;

$R^3$ is —$SO_2NR^8R^9$, —$SOR^{10}$, —$SO_2R^{11}$ and is in the para or meta position with respect to the indicated thiazole ring;

$R^4$ is hydrogen, $C_1$-$C_4$-alkoxy optionally substituted by a 5 or 6-membered heterocyclic ring containing at least one hetero atom selected from the group consisting of nitrogen, oxygen and sulphur, that ring being optionally substituted by halo, halo-$C_1$-$C_4$-alkyl, —$SO_2NH_2$, —$NR^{12}R^{13}$ or a 5 or 6-membered heterocyclic ring containing at least one hetero atom selected from the group consisting of nitrogen, oxygen and sulphur, that ring being optionally substituted by $C_1$-$C_4$-alkyl;

$R^5$ is hydrogen;

$R^6$ is hydrogen or $C_1$-$C_4$-alkyl;

$R^7$ is $C_1$-$C_4$-alkyl optionally substituted by hydroxy, di($C_1$-$C_4$-alkyl)amino or a 5 or 6-membered heterocyclic ring containing at least one hetero atom selected from the group consisting of nitrogen and oxygen, that ring being optionally substituted by $C_1$-$C_4$-alkyl;

$R^8$ is hydrogen or $C_1$-$C_4$-alkyl optionally substituted by di($C_1$-$C_4$-alkyl)amino;

$R^9$ is hydrogen, $C_1$-$C_4$-alkyl optionally substituted by hydroxy, or $C_3$-$C_5$-cycloalkyl;

$R^{10}$ is $C_1$-$C_4$-alkyl;

$R^{11}$ is $C_1$-$C_4$-alkyl;

$R^{12}$ is $C_1$-$C_4$-alkyl; and $R^{13}$ is $C_1$-$C_4$-alkyl optionally substituted by di($C_1$-$C_4$-alkyl)amino.

4. A compound according to claim 1, which is also a compound of formula XII

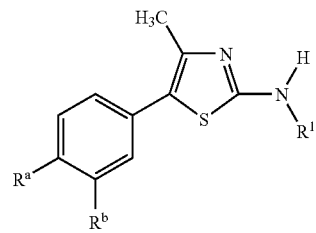

XII wherein $R^a$, $R^b$ and $R^1$ are as shown in the following table:

| $R^a$ | $R^b$ | $R^1$ |
|---|---|---|
| —$SO_2NH_2$ | H | 3-methylpyrazinyl |
| —$SO_2NH_2$ | H | 6-chloro-3-methylpyrimidinyl |
| —$SO_2NH_2$ | H | 6-methoxy-3-methylpyrimidinyl |
| —$SO_2NH_2$ | H | 6-methylpyridin-2-yl |
| —$SO_2NH_2$ | H | 5-chloro-2-methylpyridinyl |
| —$SO_2NH_2$ | H | 6-ethoxy-3-methylpyridinyl |
| —$SO_2NH_2$ | H | 3-methylpyridinyl |
| —$SO_2NH_2$ | H | 6-methoxy-3-methylpyridinyl |

-continued
| $R^a$ | $R^b$ | $R^1$ |
|---|---|---|
| —SO$_2$NH$_2$ | H | 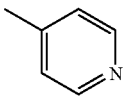 |
| —SO$_2$NH$_2$ | H | 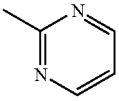 |
| —SO$_2$NH$_2$ | H | 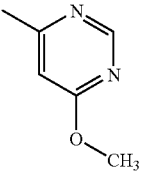 |
| —SO$_2$NH$_2$ | H | 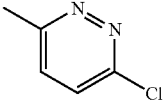 |
| —SO$_2$NH$_2$ | H | 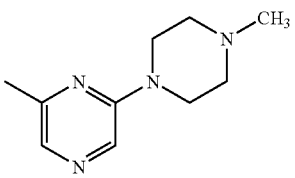 |
| —SO$_2$NH$_2$ | H | 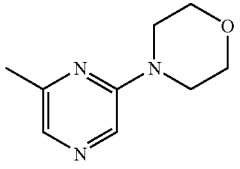 |
| —SO$_2$NH$_2$ | H | 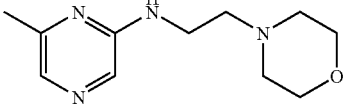 |
| —SO$_2$NH$_2$ | H | 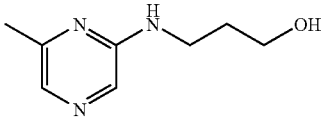 |
| —SO$_2$NH$_2$ | H | 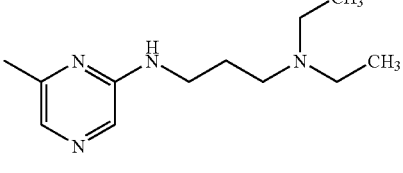 |
| 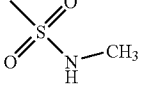 | H | 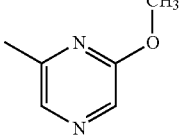 |

-continued
| R$^a$ | R$^b$ | R$^1$ |
|---|---|---|
| 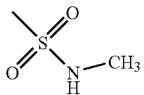 | H | 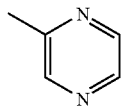 |
| 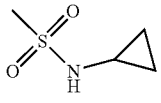 | H | 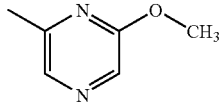 |
| 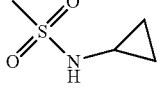 | H | 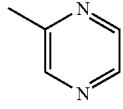 |
| —OCH$_3$ | —SO$_2$NH$_2$ | 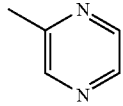 |
| —SO$_2$NH$_2$ | Cl | 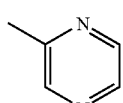 |
| —SO$_2$NH$_2$ | Cl | 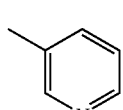 |
| —SO$_2$NH$_2$ | H | 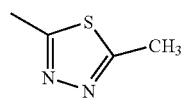 |
| —SO$_2$NH$_2$ | H | 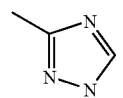 |
| 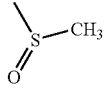 | H | 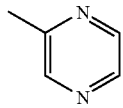 |
| 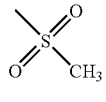 | H | 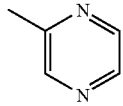 |
| 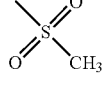 | H | 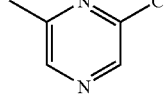 |
| 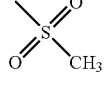 | Cl | 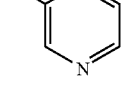 |

-continued

| R$^a$ | R$^b$ | R$^1$ |
|---|---|---|
| methylsulfonyl (S(=O)$_2$CH$_3$) | H | 5-methyl-2-(4-methylpiperazin-1-yl)pyridine |
| Cl | S(=O)$_2$CH$_3$ | 5-methyl-2-methoxypyridine |
| Cl | S(=O)$_2$NH$_2$ | 5-methylpyrazine |
| Cl | S(=O)$_2$NH-CH$_2$CH$_2$OH | 5-methylpyrazine |
| Cl | S(=O)$_2$NH-CH$_2$CH$_2$OH | 3-methyl-1H-pyrazole |
| Cl | S(=O)$_2$NH-CH$_2$CH$_2$OH | 3-methyl-1-methyl-pyrazole |
| Cl | S(=O)$_2$NH-CH$_2$CH$_2$OH | 1,3,5-trimethyl-pyrazole |
| Cl | S(=O)$_2$NH-CH$_2$CH$_2$OH | 2-methylthiazole |
| Cl | S(=O)$_2$NH-CH$_2$CH$_2$OH | 2,5-dimethylthiazole |
| Cl | S(=O)$_2$N(CH$_2$CH$_2$OH)$_2$ | 3-methyl-1H-pyrazole |
| Cl | S(=O)$_2$NH-CH$_2$CH$_2$CH$_2$N(CH$_2$CH$_3$)$_2$ | 3-methyl-1H-pyrazole |

-continued

| Rᵃ | Rᵇ | R¹ |
|---|---|---|
| H | methanesulfonyl-NH-CH₂CH₂OH | 3-methylpyrazine |
| H | methanesulfonyl-NH-CH₂CH₂OH | 3-methyl-1H-pyrazole |
| H | sulfamoyl (S(O)₂NH₂) | 3-methylpyrazine |
| H | sulfamoyl (S(O)₂NH₂) | 3-methyl-1H-pyrazole |
| H | sulfamoyl (S(O)₂NH₂) | 5-methyl-2-ethyl-1,3,4-thiadiazole |
| sulfamoyl (S(O)₂NH₂) | H | 5-methyl-1,3,4-thiadiazole |
| sulfamoyl (S(O)₂NH₂) | H | 2,5-dimethylthiazole |
| sulfamoyl (S(O)₂NH₂) | H | 3-methyl-1H-pyrazole |
| sulfamoyl (S(O)₂NH₂) | H | 2-methylthiazole |
| sulfamoyl (S(O)₂NH₂) | H | 2-methyl-4-methylthiazole |
| sulfamoyl (S(O)₂NH₂) | H | 5-methyl-1H-tetrazole |
| methanesulfonyl-NH-CH₂CH₂OH | H | 5-methyl-2-ethyl-1,3,4-thiadiazole |
| sulfamoyl (S(O)₂NH₂) | H | 5-methyl-2-(2-morpholinoethyl)-1,3,4-thiadiazole |

-continued

| R<sup>a</sup> | R<sup>b</sup> | R<sup>1</sup> |
|---|---|---|
| S(=O)(=O)NH₂ (sulfamoyl) | H | 5-methyl-1,3,4-thiadiazol-2-yl-CH₂CH₂-N(CH₃)₂ |
| S(=O)(=O)NH₂ | H | 5-methyl-1,3,4-thiadiazol-2-yl-CH₂CH₂-C(=O)OH |
| S(=O)(=O)NH₂ | H | 5-methyl-1,3,4-thiadiazol-2-yl-CH₂CH₂-C(=O)OCH₂CH₃ |
| S(=O)(=O)NH₂ | H | 5-methyl-1,3,4-thiadiazol-2-yl-CH₂-C(=O)OH |
| S(=O)(=O)CH₃ | —CF₃ | 3-methylpyrazine |
| S(=O)(=O)CH₃ | —CF₃ | 3-methyl-1H-pyrazole |
| S(=O)(=O)CH₃ | —CF₃ | 5-methyl-1,3,4-thiadiazol-2-yl-CH₂CH₂-C(=O)OH |
| S(=O)(=O)CH₃ | —CF₃ | 4-(5-methyl-1,3,4-thiadiazol-2-yl)cyclohexanecarboxylic acid |
| S(=O)(=O)CH₃ | —CF₃ | 2-(4-methylpiperazin-1-yl)-5-methyl-1,3,4-thiadiazole |
| S(=O)(=O)CH₃ | —CF₃ | 2-morpholino-5-methyl-1,3,4-thiadiazole |
| S(=O)(=O)CH₃ | —CF₃ | 2-chloro-6-methylpyrazine |

-continued

| Rᵃ | Rᵇ | R¹ |
|---|---|---|
| methylsulfonyl (—S(O)₂CH₃) | —CF₃ | 6-methyl-2-(4-methylpiperazin-1-yl)pyrazine |
| methylsulfonyl | —CF₃ | 5-methyl-2-(2-morpholinoethyl)-1,3,4-thiadiazole |
| methylsulfonyl | F | 3-methyl-1H-pyrazole |
| methylsulfonyl | F | 1,3-dimethyl-1H-pyrazole |
| methylsulfonyl | F | 4-bromo-3-methyl-1H-pyrazole |
| methylsulfonyl | 1-methyl-2-propyl-1H-imidazole | 3-methyl-1H-pyrazole |
| methylsulfonyl | 1-methyl-1H-imidazole | 3-methyl-1H-pyrazole |
| methylsulfonyl | N,N-diethyl-N',N'-dimethylethane-1,2-diamine | 3-methyl-1H-pyrazole |
| methylsulfonyl | 1,4-dimethylpiperazine | 3-methyl-1H-pyrazole |

5. A pharmaceutical composition comprising a compound according to claim 1, optionally together with a pharmaceutically acceptable diluent or carrier.

6. A pharmaceutical composition according to claim 5 further comprising one or more anti-inflammatory, bronchodilatory or antihistamine drug substances, wherein the anti-inflammatory drug substance is selected from the group consisting of steroids, LTB4 antagonists, LTD4 antagonists, dopamine receptor agonists and PDE4 inhibitors; the bronchodilatory drug substance is selected from the group consisting of anticholinergic agents, antimuscarinic agents and beta-2 adrenoceptor agonists; and the antihistamine drug substance is selected from the list consisting of cetirizine hydrochloride, acetaminophen, clemastine fumarate, promethazine, loratidine, desloratidine, diphenhydramine, and fexofenadine hydrochloride.

7. A pharmaceutical composition comprising a compound according to claim 4, optionally together with a pharmaceutically acceptable diluent or carrier.

8. A process for the preparation of a compound of formula I as defined in claim 1 that comprises the steps of:

(i) (A) reacting a compound of formula II

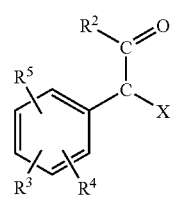

wherein $R^2$, $R^3$, $R^4$ and $R^5$ are as hereinbefore defined in claim 1 and X is halogen, with a compound of formula III

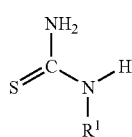

III wherein $R^1$ is as hereinbefore defined in claim 1;

(B) reacting a compound of formula IV

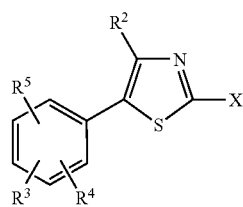

IV wherein $R^2$, $R^3$, $R^4$ and $R^5$ are as hereinbefore defined in claim 1 and X is halogen, with a compound of formula $R^1$—$NH_2$, optionally in the presence of a base;

(C) for the preparation of compounds of formula I where $R^1$ is a 5 or 6-membered heterocyclic ring containing nitrogen and optionally a further hetero atom of the group consisting of nitrogen, oxygen and sulphur that is substituted by —$NR^6R^7$, reacting a compound of formula I where $R^1$ is a 5 or 6-membered heterocyclic ring containing nitrogen and optionally a further hetero atom of the group consisting of nitrogen, oxygen and sulphur that is substituted by halo with a compound of formula V

V wherein $R^6$ and $R^7$ are as hereinbefore defined in claim 1, optionally in the presence of a base;

(D) for the preparation of compounds of formula I where $R^3$ is —$SO_2NR^8R^9$, reacting a compound of formula VI

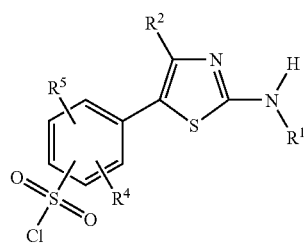

VI wherein $R^2$, $R^4$, $R^5$ and X are as hereinbefore defined in claim 1 with an amine of formula VII

VII wherein $R^8$ and $R^9$ are as hereinbefore defined in claim 1; or (E) for the preparation of compounds of formula I where one or both of $R^4$ and $R^5$ is —$NR^{12}R^{13}$, reacting a compound of formula I wherein $R^1$ and $R^2$ are hereinbefore defined, $R^3$ is —$SO_2R^{11}$ or —$SO_2NH_2$ and one or both of $R^4$ and $R^5$ is halo with a compound of formula VIII

VIII wherein $R^{12}$ and $R^{13}$ are hereinbefore defined, optionally in the presence of a base; or (F) for the preparation of compounds of formula I where one or both of $R^4$ and $R^5$ is $C_1$-$C_8$-alkoxy substituted by a 5 or 6-membered heterocyclic ring containing at least one hetero atom selected from the group consisting of nitrogen, oxygen and sulphur, reacting a compound of formula I wherein $R^1$ and $R^2$ are hereinbefore defined, $R^3$ is —$SO_2R^{11}$ or —$SO_2NH_2$ and one or both of $R^4$ and $R^5$ is halo with a compound of formula HO—$C_1$-$C_8$-alkyl-W where W is a 5 or 6-membered heterocyclic ring containing at least one hetero atom selected from the group consisting of nitrogen, oxygen and sulphur, optionally in the presence of a base; and (ii) recovering the resultant compound of formula I in free or salt form.

* * * * *